(12) United States Patent
Greener

(10) Patent No.: US 11,974,902 B2
(45) Date of Patent: *May 7, 2024

(54) VACUUM ASSISTED WOUND DRESSING

(71) Applicant: Smith & Nephew PLC, Watford (GB)

(72) Inventor: Bryan Greener, York (GB)

(73) Assignee: Smith & Nephew PLC, Watford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/204,591

(22) Filed: Jun. 1, 2023

(65) Prior Publication Data
US 2023/0338196 A1 Oct. 26, 2023

Related U.S. Application Data

(60) Continuation of application No. 17/360,893, filed on Jun. 28, 2021, now Pat. No. 11,701,266, which is a (Continued)

(30) Foreign Application Priority Data

Nov. 21, 2007 (GB) ...................................... 0722820

(51) Int. Cl.
*A61F 13/02* (2006.01)
*A61F 13/00* (2006.01)
(Continued)

(52) U.S. Cl.
CPC .... *A61F 13/0206* (2013.01); *A61F 13/00068* (2013.01); *A61F 13/0209* (2013.01);
(Continued)

(58) Field of Classification Search
CPC .............. A61M 1/0092; A61M 1/0088; A61M 1/0049; A61M 39/24; A61F 13/0068;
(Continued)

(56) References Cited

U.S. PATENT DOCUMENTS 695,270 A 3/1902 Beringer
1,480,562 A 1/1924 Hugo et al.
(Continued)

FOREIGN PATENT DOCUMENTS

CA 2198243 A1 2/1996
CA 2367460 A1 10/2000
(Continued)

OTHER PUBLICATIONS

US 6,216,701 B1, 04/2001, Heaton et al. (withdrawn)
(Continued)

*Primary Examiner* — Guy K Townsend
(74) *Attorney, Agent, or Firm* — Knobbe, Martens, Olson & Bear, LLP

(57) ABSTRACT

Apparatus for the application of topical negative pressure therapy to a wound site is described, the apparatus comprising: a wound contacting element for retaining wound exudate fluid therein; a wound covering element that provides a substantially airtight seal over the wound contacting element and wound site; a vacuum connection tube connecting a wound cavity to a vacuum source; and a vacuum source connected to a distal end of the vacuum connection tube.

20 Claims, 3 Drawing Sheets

Related U.S. Application Data continuation of application No. 15/973,111, filed on May 7, 2018, now Pat. No. 11,045,598, which is a division of application No. 14/254,807, filed on Apr. 16, 2014, now Pat. No. 9,962,474, which is a continuation of application No. 12/744,055, filed as application No. PCT/GB2008/051088 on Nov. 20, 2008, now Pat. No. 8,715,256.

(51) Int. Cl.
| | | |
|---|---|---|
| *A61F 13/0203* | (2024.01) | |
| *A61F 13/0206* | (2024.01) | |
| *A61M 1/00* | (2006.01) | |
| *A61M 39/24* | (2006.01) | |

(52) U.S. Cl.
CPC ...... *A61F 13/0216* (2013.01); *A61F 13/0226* (2013.01); *A61M 1/964* (2021.05); *A61M 1/985* (2021.05); *A61F 2013/00536* (2013.01); *A61F 2013/0094* (2013.01); *A61M 1/78* (2021.05); *A61M 39/24* (2013.01)

(58) Field of Classification Search
CPC .............. A61F 13/0206; A61F 13/0226; A61F 13/0216; A61F 2013/00536; A61F 2013/0094

See application file for complete search history.

(56) References Cited

U.S. PATENT DOCUMENTS

| | | |
|---|---|---|
| 2,280,915 A | 4/1942 | Johnson |
| 2,367,690 A | 1/1945 | Purdy |
| 2,568,933 A | 9/1951 | Robbins |
| 2,632,443 A | 3/1953 | Lesher |
| 2,682,873 A | 7/1954 | Idnis et al. |
| 2,910,763 A | 11/1959 | Lauterbach |
| 3,115,138 A | 12/1963 | McElvenny et al. |
| 3,367,332 A | 2/1968 | Groves |
| 3,486,504 A | 12/1969 | Austin, Jr. et al. |
| 3,572,340 A | 3/1971 | Lloyd et al. |
| 3,610,238 A | 10/1971 | Rich, Jr. |
| 3,874,387 A | 4/1975 | Barbieri |
| 3,972,328 A | 8/1976 | Chen |
| 3,993,080 A | 11/1976 | Loseff |
| 4,029,598 A | 6/1977 | Neisius et al. |
| RE29,319 E | 7/1977 | Nordby et al. |
| 4,102,342 A | 7/1978 | Akiyama et al. |
| 4,112,947 A | 9/1978 | Nehring |
| 4,136,696 A | 1/1979 | Nehring |
| 4,184,510 A | 1/1980 | Murry et al. |
| 4,217,894 A | 8/1980 | Franetzki |
| 4,219,019 A | 8/1980 | Coates |
| 4,224,945 A | 9/1980 | Cohen |
| 4,250,882 A | 2/1981 | Adair |
| 4,316,466 A | 2/1982 | Babb |
| 4,382,441 A | 5/1983 | Svedman |
| 4,465,485 A | 8/1984 | Kashmer et al. |
| 4,468,227 A | 8/1984 | Jensen |
| 4,525,166 A | 6/1985 | Leclerc |
| 4,534,356 A | 8/1985 | Papadakis |
| 4,551,141 A | 11/1985 | McNeil |
| 4,573,965 A | 3/1986 | Russo |
| 4,608,041 A | 8/1986 | Nielsen |
| 4,655,754 A | 4/1987 | Richmond et al. |
| 4,655,766 A | 4/1987 | Theeuwes et al. |
| 4,681,562 A | 7/1987 | Beck et al. |
| 4,710,165 A | 12/1987 | McNeil et al. |
| 4,728,499 A | 3/1988 | Fehder |
| 4,778,446 A | 10/1988 | Jensen |
| 4,778,456 A | 10/1988 | Lokken |
| 4,792,328 A | 12/1988 | Beck et al. |
| 4,795,435 A | 1/1989 | Steer |
| 4,813,942 A | 3/1989 | Alvarez |
| 4,820,284 A | 4/1989 | Hauri |
| 4,826,494 A | 5/1989 | Richmond et al. |
| 4,828,546 A | 5/1989 | McNeil et al. |
| 4,921,488 A | 5/1990 | Maitz et al. |
| 4,936,834 A | 6/1990 | Beck et al. |
| 4,950,483 A | 8/1990 | Ksander et al. |
| 4,969,880 A | 11/1990 | Zamierowski |
| 4,972,829 A | 11/1990 | Knerr |
| 4,979,944 A | 12/1990 | Luzsicza |
| 4,994,022 A | 2/1991 | Steffler et al. |
| 5,010,115 A | 4/1991 | Grisoni |
| 5,055,198 A | 10/1991 | Shettigar |
| 5,056,510 A | 10/1991 | Gilman |
| 5,060,642 A | 10/1991 | Gilman |
| 5,073,172 A | 12/1991 | Fell |
| 5,080,493 A | 1/1992 | McKown et al. |
| 5,100,396 A | 3/1992 | Zamierowski |
| 5,134,994 A | 8/1992 | Say |
| 5,149,331 A | 9/1992 | Ferdman et al. |
| 5,152,757 A | 10/1992 | Eriksson |
| 5,167,613 A | 12/1992 | Karami et al. |
| 5,176,663 A | 1/1993 | Svedman et al. |
| 5,181,905 A | 1/1993 | Flam |
| 5,215,519 A | 6/1993 | Shettigar |
| 5,234,419 A | 8/1993 | Bryant et al. |
| 5,238,732 A | 8/1993 | Krishnan |
| 5,249,709 A | 10/1993 | Duckworth et al. |
| 5,261,893 A | 11/1993 | Zamierowski |
| 5,266,326 A | 11/1993 | Barry et al. |
| 5,266,928 A | 11/1993 | Johnson |
| 5,279,608 A | 1/1994 | Cherif Cheikh |
| 5,328,614 A | 7/1994 | Matsumura |
| 5,333,760 A | 8/1994 | Simmen |
| 5,358,494 A | 10/1994 | Svedman |
| 5,380,280 A | 1/1995 | Peterson |
| 5,437,651 A | 8/1995 | Todd et al. |
| 5,445,604 A | 8/1995 | Lang |
| 5,456,745 A | 10/1995 | Roreger et al. |
| 5,489,280 A | 2/1996 | Russell |
| 5,498,338 A | 3/1996 | Kruger et al. |
| 5,527,293 A | 6/1996 | Zamierowski |
| 5,536,233 A | 7/1996 | Khouri |
| 5,549,584 A * | 8/1996 | Gross .................... A61M 1/915 604/319 |
| 5,562,107 A | 10/1996 | Lavender et al. |
| 5,582,596 A | 12/1996 | Fukunaga et al. |
| 5,583,114 A | 12/1996 | Barrows et al. |
| 5,609,271 A | 3/1997 | Keller et al. |
| 5,612,050 A | 3/1997 | Rowe et al. |
| 5,624,423 A | 4/1997 | Anjur et al. |
| 5,632,731 A | 5/1997 | Patel |
| 5,636,643 A | 6/1997 | Argenta et al. |
| 5,643,189 A | 7/1997 | Masini |
| 5,645,081 A | 7/1997 | Argenta et al. |
| 5,660,823 A | 8/1997 | Chakrabarti et al. |
| 5,662,583 A | 9/1997 | Khouri |
| 5,676,634 A | 10/1997 | Khouri |
| 5,678,564 A * | 10/1997 | Lawrence ............... A61F 5/455 600/573 |
| 5,695,445 A | 12/1997 | Khouri |
| 5,700,477 A * | 12/1997 | Rosenthal ............... A61L 27/56 514/777 |
| 5,701,917 A | 12/1997 | Khouri |
| 5,707,499 A | 1/1998 | Joshi et al. |
| 5,717,030 A | 2/1998 | Dunn et al. |
| 5,733,337 A | 3/1998 | Carr, Jr. et al. |
| 5,747,064 A | 5/1998 | Burnett et al. |
| 5,759,570 A | 6/1998 | Arnold |
| 5,776,098 A | 7/1998 | Silver et al. |
| 5,776,193 A | 7/1998 | Kwan et al. |
| 5,785,688 A | 7/1998 | Joshi et al. |
| 5,817,145 A | 10/1998 | Augustine et al. |
| 5,830,496 A | 11/1998 | Freeman |
| 5,833,646 A | 11/1998 | Masini |
| 5,834,007 A | 11/1998 | Kubota |
| 5,843,011 A | 12/1998 | Lucas |
| 5,852,126 A | 12/1998 | Barnard et al. |
| 5,868,933 A | 2/1999 | Patrick et al. |
| 5,874,500 A | 2/1999 | Rhee et al. |

(56) References Cited

U.S. PATENT DOCUMENTS

| | | | |
|---|---|---|---|
| 5,876,611 A | 3/1999 | Shettigar | |
| 5,928,265 A | 7/1999 | Fleischmann | |
| 5,945,115 A | 8/1999 | Dunn et al. | |
| 5,962,010 A | 10/1999 | Greff et al. | |
| 5,964,723 A | 10/1999 | Augustine | |
| 5,998,472 A | 12/1999 | Berger et al. | |
| 6,010,527 A | 1/2000 | Augustine et al. | |
| 6,013,097 A | 1/2000 | Augustine et al. | |
| 6,071,267 A | 6/2000 | Zamierowski | |
| 6,093,160 A | 7/2000 | Augustine et al. | |
| 6,103,951 A | 8/2000 | Freeman | |
| 6,110,197 A | 8/2000 | Augustine et al. | |
| 6,117,111 A | 9/2000 | Fleischmann | |
| 6,135,116 A | 10/2000 | Vogel et al. | |
| D434,150 S | 11/2000 | Tumey et al. | |
| 6,142,982 A * | 11/2000 | Hunt | A61M 1/82 |
| | | | 604/313 |
| 6,143,352 A | 11/2000 | Clark et al. | |
| 6,165,201 A | 12/2000 | Sawhney et al. | |
| 6,168,788 B1 | 1/2001 | Wortham | |
| 6,168,800 B1 | 1/2001 | Dobos et al. | |
| 6,176,307 B1 | 1/2001 | Danos et al. | |
| 6,214,332 B1 | 4/2001 | Askill et al. | |
| 6,225,523 B1 | 5/2001 | Masini | |
| 6,248,084 B1 | 6/2001 | Augustine et al. | |
| 6,252,129 B1 | 6/2001 | Coffee | |
| 6,254,567 B1 | 7/2001 | Treu et al. | |
| 6,255,552 B1 | 7/2001 | Cummings et al. | |
| 6,257,847 B1 | 7/2001 | Silver et al. | |
| 6,261,283 B1 | 7/2001 | Morgan et al. | |
| 6,267,740 B1 | 7/2001 | Augustine et al. | |
| 6,287,521 B1 | 9/2001 | Quay et al. | |
| 6,291,050 B1 | 9/2001 | Cree et al. | |
| 6,293,917 B1 | 9/2001 | Augustine et al. | |
| 6,345,623 B1 | 2/2002 | Heaton et al. | |
| 6,383,163 B1 | 5/2002 | Kelly et al. | |
| 6,391,294 B1 | 5/2002 | Dettmar et al. | |
| 6,398,761 B1 | 6/2002 | Bills et al. | |
| 6,398,767 B1 | 6/2002 | Fleischmann | |
| 6,402,724 B1 | 6/2002 | Smith et al. | |
| 6,440,167 B2 | 8/2002 | Shimizu | |
| 6,447,802 B2 | 9/2002 | Sessions et al. | |
| 6,450,773 B1 | 9/2002 | Upton | |
| 6,458,109 B1 | 10/2002 | Henley et al. | |
| 6,465,708 B1 | 10/2002 | Augustine | |
| 6,468,295 B2 | 10/2002 | Augustine et al. | |
| 6,471,685 B1 | 10/2002 | Johnson | |
| 6,471,982 B1 | 10/2002 | Lydon et al. | |
| 6,481,986 B1 | 11/2002 | Silver et al. | |
| 6,482,491 B1 | 11/2002 | Samuelsen et al. | |
| 6,486,285 B2 | 11/2002 | Fujita | |
| 6,491,684 B1 | 12/2002 | Joshi et al. | |
| 6,495,127 B1 | 12/2002 | Wallace et al. | |
| 6,500,112 B1 | 12/2002 | Khouri | |
| 6,509,031 B1 | 1/2003 | Miller et al. | |
| 6,521,251 B2 | 2/2003 | Askill et al. | |
| 6,547,467 B2 | 4/2003 | Quintero | |
| 6,547,756 B1 | 4/2003 | Greter et al. | |
| 6,553,998 B2 * | 4/2003 | Heaton | A61M 1/912 |
| | | | 602/42 |
| 6,575,940 B1 | 6/2003 | Levinson et al. | |
| 6,580,012 B1 | 6/2003 | Augustine et al. | |
| 6,596,704 B1 | 7/2003 | Court et al. | |
| 6,599,262 B1 | 7/2003 | Masini | |
| 6,626,891 B2 | 9/2003 | Ohmstede | |
| 6,627,216 B2 | 9/2003 | Brandt et al. | |
| 6,629,774 B1 | 10/2003 | Gruendeman | |
| 6,638,270 B2 | 10/2003 | Johnson | |
| 6,648,862 B2 | 11/2003 | Watson | |
| 6,673,028 B1 | 1/2004 | Argenta et al. | |
| 6,676,610 B2 | 1/2004 | Morton et al. | |
| 6,676,631 B1 | 1/2004 | Greter | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| 6,699,213 B1 | 3/2004 | Annis et al. | |
| 6,730,299 B1 | 5/2004 | Tayot et al. | |
| 6,752,794 B2 * | 6/2004 | Lockwood | A61M 1/915 |
| | | | 604/313 |
| 6,755,807 B2 * | 6/2004 | Risk, Jr. | A61M 35/00 |
| | | | 604/319 |
| 6,764,462 B2 | 7/2004 | Risk, Jr. et al. | |
| 6,767,334 B1 | 7/2004 | Randolph | |
| 6,775,807 B2 | 8/2004 | Lowther et al. | |
| 6,787,682 B2 | 9/2004 | Gilman | |
| 6,790,438 B1 | 9/2004 | Constancis et al. | |
| 6,800,074 B2 | 10/2004 | Henley et al. | |
| 6,808,517 B2 | 10/2004 | Greter et al. | |
| 6,814,079 B2 | 11/2004 | Heaton et al. | |
| 6,824,533 B2 | 11/2004 | Risk, Jr. et al. | |
| 6,855,135 B2 | 2/2005 | Lockwood et al. | |
| 6,856,821 B2 | 2/2005 | Johnson | |
| 6,936,037 B2 | 8/2005 | Bubb et al. | |
| 6,951,553 B2 | 10/2005 | Bubb et al. | |
| 6,960,179 B2 | 11/2005 | Gura | |
| 6,977,323 B1 | 12/2005 | Swenson | |
| 6,979,324 B2 | 12/2005 | Bybordi et al. | |
| 6,987,209 B2 | 1/2006 | Augustine et al. | |
| 6,994,702 B1 | 2/2006 | Johnson | |
| 6,997,897 B1 | 2/2006 | Silver et al. | |
| 7,004,915 B2 | 2/2006 | Boynton et al. | |
| 7,008,400 B2 | 3/2006 | Silver et al. | |
| 7,022,113 B2 | 4/2006 | Lockwood et al. | |
| 7,067,709 B2 | 6/2006 | Murata et al. | |
| 7,070,584 B2 | 7/2006 | Johnson et al. | |
| 7,077,832 B2 | 7/2006 | Fleischmann | |
| 7,087,806 B2 | 8/2006 | Scheinberg et al. | |
| 7,108,683 B2 | 9/2006 | Zamierowski | |
| 7,117,869 B2 | 10/2006 | Heaton et al. | |
| 7,118,545 B2 | 10/2006 | Boyde | |
| 7,122,046 B2 | 10/2006 | Augustine et al. | |
| 7,128,735 B2 | 10/2006 | Weston | |
| 7,129,210 B2 | 10/2006 | Lowinger et al. | |
| 7,141,714 B2 | 11/2006 | Nielsen | |
| 7,182,085 B1 | 2/2007 | Larsen et al. | |
| 7,195,624 B2 | 3/2007 | Lockwood et al. | |
| 7,214,202 B1 | 5/2007 | Vogel et al. | |
| 7,216,651 B2 | 5/2007 | Argenta et al. | |
| 7,238,850 B2 | 7/2007 | Shimanuki | |
| 7,255,681 B1 | 8/2007 | Silver et al. | |
| 7,273,054 B2 | 9/2007 | Heaton et al. | |
| 7,279,612 B1 | 10/2007 | Heaton et al. | |
| 7,303,757 B2 | 12/2007 | Schankereli et al. | |
| 7,316,672 B1 | 1/2008 | Hunt et al. | |
| 7,335,809 B2 | 2/2008 | Riesinger | |
| 7,338,482 B2 | 3/2008 | Lockwood et al. | |
| 7,361,184 B2 | 4/2008 | Joshi | |
| 7,381,211 B2 | 6/2008 | Zamierowski | |
| 7,381,859 B2 | 6/2008 | Hunt et al. | |
| 7,438,705 B2 | 10/2008 | Karpowicz et al. | |
| 7,470,830 B2 | 12/2008 | Sigurjonsson et al. | |
| 7,485,112 B2 | 2/2009 | Karpowicz et al. | |
| 7,494,482 B2 | 2/2009 | Orgill et al. | |
| 7,503,910 B2 | 3/2009 | Adahan | |
| 7,507,870 B2 | 3/2009 | Nielsen et al. | |
| 7,524,286 B2 | 4/2009 | Johnson | |
| 7,524,315 B2 | 4/2009 | Blott et al. | |
| 7,534,240 B1 | 5/2009 | Johnson | |
| 7,534,927 B2 | 5/2009 | Lockwood et al. | |
| 7,569,742 B2 | 8/2009 | Haggstrom et al. | |
| 7,601,129 B2 | 10/2009 | Aali | |
| 7,605,298 B2 | 10/2009 | Bechert et al. | |
| 7,611,500 B1 | 11/2009 | Lina et al. | |
| 7,612,247 B2 | 11/2009 | Oyaski | |
| 7,615,036 B2 | 11/2009 | Joshi et al. | |
| 7,622,629 B2 | 11/2009 | Aali | |
| 7,625,362 B2 | 12/2009 | Boehringer et al. | |
| 7,645,253 B2 | 1/2010 | Gura et al. | |
| 7,645,269 B2 | 1/2010 | Zamierowski | |
| 7,670,323 B2 | 3/2010 | Hunt et al. | |
| 7,678,090 B2 | 3/2010 | Risk, Jr. et al. | |
| 7,699,823 B2 | 4/2010 | Haggstrom et al. | |
| 7,699,830 B2 | 4/2010 | Martin | |
| 7,700,819 B2 | 4/2010 | Ambrosio et al. | |

(56) References Cited

U.S. PATENT DOCUMENTS

| | | | |
|---|---|---|---|
| 7,708,724 B2 * | 5/2010 | Weston | A61M 1/985 604/304 |
| 7,717,313 B2 | 5/2010 | Criscuolo et al. | |
| 7,718,249 B2 | 5/2010 | Russell et al. | |
| 7,722,582 B2 | 5/2010 | Lina et al. | |
| 7,731,702 B2 | 6/2010 | Bybordi et al. | |
| 7,745,681 B1 | 6/2010 | Ferguson | |
| 7,749,531 B2 | 7/2010 | Booher | |
| 7,753,894 B2 | 7/2010 | Blott et al. | |
| 7,754,936 B2 | 7/2010 | Heaton et al. | |
| 7,754,937 B2 | 7/2010 | Boehringer et al. | |
| 7,758,514 B2 | 7/2010 | Grigoryants et al. | |
| 7,758,554 B2 | 7/2010 | Lina et al. | |
| 7,759,537 B2 | 7/2010 | Bishop et al. | |
| 7,759,538 B2 | 7/2010 | Fleischmann | |
| 7,759,539 B2 | 7/2010 | Shaw et al. | |
| 7,763,000 B2 | 7/2010 | Risk, Jr. et al. | |
| 7,763,769 B2 | 7/2010 | Johnson et al. | |
| 7,775,998 B2 | 8/2010 | Riesinger | |
| 7,776,028 B2 | 8/2010 | Miller et al. | |
| 7,779,625 B2 | 8/2010 | Joshi et al. | |
| 7,790,945 B1 * | 9/2010 | Watson, Jr. | A61M 27/00 604/289 |
| 7,790,946 B2 | 9/2010 | Mulligan | |
| 7,794,438 B2 | 9/2010 | Henley et al. | |
| 7,794,450 B2 | 9/2010 | Blott et al. | |
| 7,803,980 B2 | 9/2010 | Griffiths et al. | |
| 7,811,269 B2 | 10/2010 | Boynton et al. | |
| 7,812,212 B2 | 10/2010 | Propp et al. | |
| 7,815,616 B2 | 10/2010 | Boehringer et al. | |
| 7,816,577 B2 | 10/2010 | Aali | |
| 7,825,289 B2 | 11/2010 | Vess | |
| 7,828,782 B2 * | 11/2010 | Suzuki | A61M 25/10 604/93.01 |
| 7,838,716 B2 | 11/2010 | De Luis et al. | |
| 7,838,717 B2 | 11/2010 | Haggstrom et al. | |
| 7,846,141 B2 | 12/2010 | Weston | |
| 7,857,806 B2 | 12/2010 | Karpowicz et al. | |
| 7,858,838 B2 | 12/2010 | Holm et al. | |
| 7,862,339 B2 | 1/2011 | Mulligan | |
| 7,862,831 B2 | 1/2011 | Wang et al. | |
| 7,867,206 B2 | 1/2011 | Lockwood et al. | |
| 7,880,050 B2 | 2/2011 | Robinson et al. | |
| 7,883,494 B2 | 2/2011 | Martin | |
| 7,884,258 B2 | 2/2011 | Boehringer et al. | |
| 7,886,746 B2 | 2/2011 | Heaton et al. | |
| 7,896,823 B2 | 3/2011 | Mangrum et al. | |
| 7,896,856 B2 | 3/2011 | Petrosenko et al. | |
| 7,909,805 B2 * | 3/2011 | Weston | A61M 1/784 604/313 |
| 7,910,135 B2 | 3/2011 | St. John et al. | |
| 7,910,791 B2 | 3/2011 | Coffey | |
| 7,922,703 B2 | 4/2011 | Riesinger | |
| 7,927,318 B2 | 4/2011 | Risk, Jr. et al. | |
| 7,931,630 B2 | 4/2011 | Nishtala et al. | |
| 7,951,100 B2 | 5/2011 | Hunt et al. | |
| 7,951,124 B2 | 5/2011 | Boehringer et al. | |
| 7,959,624 B2 | 6/2011 | Riesinger | |
| 7,964,766 B2 | 6/2011 | Blott et al. | |
| 7,976,519 B2 | 7/2011 | Bubb et al. | |
| D642,594 S | 8/2011 | Mattson et al. | |
| 7,988,680 B2 | 8/2011 | Lockwood et al. | |
| 7,998,125 B2 | 8/2011 | Weston | |
| 8,007,164 B2 | 8/2011 | Miyano et al. | |
| 8,007,257 B2 | 8/2011 | Heaton et al. | |
| 8,007,481 B2 | 8/2011 | Schuessler et al. | |
| 8,012,169 B2 | 9/2011 | Joshi | |
| 8,021,348 B2 | 9/2011 | Risk, Jr. et al. | |
| 8,022,266 B2 | 9/2011 | Boehringer et al. | |
| 8,025,650 B2 | 9/2011 | Anderson et al. | |
| 8,034,037 B2 | 10/2011 | Adams et al. | |
| 8,034,038 B2 | 10/2011 | Biggie et al. | |
| 8,062,272 B2 * | 11/2011 | Weston | A61M 1/98 604/313 |
| 8,062,273 B2 | 11/2011 | Weston | |
| 8,062,331 B2 | 11/2011 | Zamierowski | |
| 8,080,702 B2 | 12/2011 | Blott et al. | |
| 8,084,663 B2 * | 12/2011 | Watson, Jr. | A61F 13/0203 604/289 |
| 8,092,441 B2 | 1/2012 | Sugito | |
| 8,097,272 B2 | 1/2012 | Addison | |
| 8,100,887 B2 | 1/2012 | Weston et al. | |
| 8,105,295 B2 | 1/2012 | Blott et al. | |
| 8,118,794 B2 | 2/2012 | Weston | |
| 8,119,160 B2 | 2/2012 | Looney et al. | |
| 8,128,615 B2 | 3/2012 | Blott et al. | |
| 8,133,211 B2 | 3/2012 | Cavanaugh, II et al. | |
| 8,147,468 B2 | 4/2012 | Barta et al. | |
| 8,152,785 B2 | 4/2012 | Vitaris | |
| 8,158,844 B2 | 4/2012 | McNeil | |
| 8,162,907 B2 | 4/2012 | Heagle | |
| 8,162,909 B2 | 4/2012 | Blott et al. | |
| 8,168,848 B2 | 5/2012 | Lockwood et al. | |
| 8,188,331 B2 | 5/2012 | Barta et al. | |
| 8,192,409 B2 | 6/2012 | Hardman et al. | |
| 8,202,261 B2 | 6/2012 | Kazala, Jr. et al. | |
| 8,207,392 B2 | 6/2012 | Haggstrom et al. | |
| 8,211,071 B2 | 7/2012 | Mormino et al. | |
| 8,215,929 B2 | 7/2012 | Shen et al. | |
| 8,226,942 B2 | 7/2012 | Charier et al. | |
| 8,235,955 B2 | 8/2012 | Blott et al. | |
| 8,235,972 B2 | 8/2012 | Adahan | |
| 8,241,261 B2 | 8/2012 | Randolph et al. | |
| 8,246,606 B2 | 8/2012 | Stevenson et al. | |
| 8,251,979 B2 | 8/2012 | Malhi | |
| 8,257,326 B2 | 9/2012 | Vitaris | |
| 8,257,327 B2 | 9/2012 | Blott et al. | |
| 8,257,328 B2 | 9/2012 | Augustine et al. | |
| 8,267,908 B2 | 9/2012 | Coulthard | |
| 8,273,368 B2 | 9/2012 | Ambrosio et al. | |
| 8,282,611 B2 | 10/2012 | Weston | |
| 8,294,586 B2 | 10/2012 | Pidgeon et al. | |
| 8,303,552 B2 | 11/2012 | Weston | |
| 8,308,714 B2 | 11/2012 | Weston et al. | |
| 8,317,774 B2 | 11/2012 | Adahan | |
| 8,323,264 B2 | 12/2012 | Weston et al. | |
| 8,338,402 B2 | 12/2012 | Fry et al. | |
| 8,348,910 B2 | 1/2013 | Blott et al. | |
| 8,372,049 B2 | 2/2013 | Jaeb et al. | |
| 8,372,050 B2 | 2/2013 | Jaeb et al. | |
| 8,376,972 B2 | 2/2013 | Fleischmann | |
| 8,382,731 B2 | 2/2013 | Johannison | |
| 8,398,614 B2 | 3/2013 | Blott et al. | |
| 8,399,730 B2 | 3/2013 | Kazala, Jr. et al. | |
| 8,404,921 B2 | 3/2013 | Lee et al. | |
| D679,819 S | 4/2013 | Peron | |
| D679,820 S | 4/2013 | Peron | |
| 8,410,189 B2 | 4/2013 | Carnahan et al. | |
| 8,425,478 B2 | 4/2013 | Olson | |
| 8,444,612 B2 | 5/2013 | Patel et al. | |
| 8,449,509 B2 * | 5/2013 | Weston | A61M 1/782 604/319 |
| 8,460,225 B2 | 6/2013 | Wickstrom | |
| 8,460,255 B2 | 6/2013 | Joshi et al. | |
| 8,494,349 B2 | 7/2013 | Gordon | |
| 8,506,554 B2 | 8/2013 | Adahan | |
| 8,513,481 B2 | 8/2013 | Gergely et al. | |
| 8,535,283 B2 | 9/2013 | Heaton et al. | |
| 8,535,296 B2 | 9/2013 | Blott et al. | |
| 8,545,466 B2 | 10/2013 | Andresen et al. | |
| 8,556,871 B2 | 10/2013 | Mormino et al. | |
| 8,569,566 B2 | 10/2013 | Blott et al. | |
| 8,628,505 B2 | 1/2014 | Weston | |
| 8,641,691 B2 | 2/2014 | Fink et al. | |
| 8,663,198 B2 | 3/2014 | Buan et al. | |
| 8,679,079 B2 | 3/2014 | Heaton et al. | |
| 8,708,998 B2 | 4/2014 | Weston et al. | |
| 8,715,256 B2 * | 5/2014 | Greener | A61M 1/964 604/319 |
| 8,721,606 B2 | 5/2014 | Simmons et al. | |
| 8,728,044 B2 | 5/2014 | Coulthard et al. | |
| 8,753,670 B2 | 6/2014 | Delmotte | |
| 8,764,732 B2 | 7/2014 | Hartwell | |

(56) References Cited

U.S. PATENT DOCUMENTS

| | | |
|---|---|---|
| 8,784,393 B2 | 7/2014 | Weston et al. |
| 8,795,243 B2 * | 8/2014 | Weston .................... A61M 1/98 604/304 |
| 8,795,244 B2 | 8/2014 | Randolph et al. |
| 8,795,635 B2 | 8/2014 | Tamarkin et al. |
| 8,795,713 B2 | 8/2014 | Makower et al. |
| 8,795,800 B2 | 8/2014 | Evans |
| 8,808,274 B2 | 8/2014 | Hartwell |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,843,327 B2 | 9/2014 | Vernon-Harcourt et al. |
| 8,864,748 B2 | 10/2014 | Coulthard et al. |
| 8,911,681 B2 | 12/2014 | Song et al. |
| 8,926,592 B2 | 1/2015 | Blott et al. |
| 8,956,336 B2 | 2/2015 | Haggstrom et al. |
| 8,968,773 B2 | 3/2015 | Thomas et al. |
| 9,012,714 B2 | 4/2015 | Fleischmann |
| 9,028,872 B2 | 5/2015 | Gaserod et al. |
| 9,033,942 B2 | 5/2015 | Vess |
| 9,044,579 B2 | 6/2015 | Blott et al. |
| 9,061,095 B2 | 6/2015 | Adie et al. |
| 9,127,665 B2 | 9/2015 | Locke et al. |
| 9,168,180 B2 * | 10/2015 | Ha .................... A61F 13/00063 |
| 9,168,330 B2 | 10/2015 | Joshi et al. |
| 9,199,012 B2 | 12/2015 | Vitaris et al. |
| 9,220,822 B2 | 12/2015 | Hartwell |
| 9,272,080 B2 * | 3/2016 | Weston ............... A61F 13/0216 |
| 9,302,033 B2 | 4/2016 | Riesinger |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,414,968 B2 | 8/2016 | Heagle |
| 9,421,309 B2 | 8/2016 | Robinson et al. |
| 9,446,178 B2 | 9/2016 | Blott et al. |
| 9,452,248 B2 | 9/2016 | Blott et al. |
| 9,925,313 B2 * | 3/2018 | Weston .................... A61M 1/98 |
| 9,962,474 B2 * | 5/2018 | Greener ............... A61M 1/964 |
| 10,207,035 B2 * | 2/2019 | Weston .................... A61M 1/98 |
| 10,369,058 B2 * | 8/2019 | Ha ........................ A61F 13/025 |
| 11,045,598 B2 * | 6/2021 | Greener .............. A61F 13/0226 |
| 11,701,266 B2 * | 7/2023 | Greener ................ A61M 1/985 604/319 |
| 2001/0004082 A1 | 6/2001 | Keller et al. |
| 2001/0029956 A1 * | 10/2001 | Argenta .............. A61F 13/0226 602/42 |
| 2001/0031911 A1 | 10/2001 | Khouri |
| 2001/0034499 A1 | 10/2001 | Sessions et al. |
| 2001/0043913 A1 | 11/2001 | Spaans et al. |
| 2001/0043943 A1 * | 11/2001 | Coffey .................... A61L 15/44 602/50 |
| 2002/0002209 A1 | 1/2002 | Mork |
| 2002/0026133 A1 | 2/2002 | Augustine et al. |
| 2002/0038826 A1 | 4/2002 | Hurray et al. |
| 2002/0068913 A1 | 6/2002 | Fleischmann |
| 2002/0082567 A1 | 6/2002 | Lockwood et al. |
| 2002/0115952 A1 * | 8/2002 | Johnson ................. A61M 1/985 602/41 |
| 2002/0122771 A1 | 9/2002 | Holland et al. |
| 2002/0143286 A1 | 10/2002 | Tumey |
| 2002/0145007 A1 | 10/2002 | Sawhney et al. |
| 2002/0161317 A1 | 10/2002 | Risk et al. |
| 2002/0183702 A1 | 12/2002 | Henley et al. |
| 2002/0187182 A1 | 12/2002 | Kramer et al. |
| 2002/0198490 A1 | 12/2002 | Wirt et al. |
| 2003/0014025 A1 | 1/2003 | Allen et al. |
| 2003/0021775 A1 | 1/2003 | Freeman |
| 2003/0023286 A1 | 1/2003 | Augustine et al. |
| 2003/0040478 A1 | 2/2003 | Drucker et al. |
| 2003/0045825 A1 | 3/2003 | Etheredge, III |
| 2003/0064190 A1 | 4/2003 | Carte et al. |
| 2003/0069529 A1 | 4/2003 | Augustine et al. |
| 2003/0069535 A1 | 4/2003 | Shalaby |
| 2003/0069536 A1 | 4/2003 | Greter et al. |
| 2003/0069563 A1 | 4/2003 | Johnson |
| 2003/0125646 A1 | 7/2003 | Whitlock |
| 2003/0125649 A1 | 7/2003 | McIntosh et al. |
| 2003/0143189 A1 | 7/2003 | Askill et al. |
| 2003/0144619 A1 | 7/2003 | Augustine |
| 2003/0153860 A1 | 8/2003 | Nielsen et al. |
| 2003/0171675 A1 | 9/2003 | Rosenberg |
| 2003/0175798 A1 | 9/2003 | Raees et al. |
| 2003/0183653 A1 | 10/2003 | Bills |
| 2003/0188754 A1 | 10/2003 | Heaton et al. |
| 2003/0208149 A1 * | 11/2003 | Coffey ..................... A61L 15/32 602/48 |
| 2003/0212357 A1 * | 11/2003 | Pace ....................... A61M 1/85 602/41 |
| 2003/0212431 A1 | 11/2003 | Brady et al. |
| 2003/0219469 A1 | 11/2003 | Johnson et al. |
| 2003/0225347 A1 * | 12/2003 | Argenta ................. A61B 17/88 601/6 |
| 2004/0019342 A1 | 1/2004 | Nagasuna et al. |
| 2004/0024351 A1 | 2/2004 | Greter et al. |
| 2004/0033466 A1 | 2/2004 | Shellard et al. |
| 2004/0037897 A1 | 2/2004 | Benjamin et al. |
| 2004/0039391 A1 | 2/2004 | Argenta et al. |
| 2004/0039415 A1 | 2/2004 | Zamierowski |
| 2004/0049187 A1 | 3/2004 | Burnett et al. |
| 2004/0054338 A1 | 3/2004 | Bybordi et al. |
| 2004/0057855 A1 | 3/2004 | Gerlach et al. |
| 2004/0064111 A1 | 4/2004 | Lockwood et al. |
| 2004/0064132 A1 | 4/2004 | Boehringer et al. |
| 2004/0073151 A1 * | 4/2004 | Weston .................. A61M 1/982 602/41 |
| 2004/0073152 A1 | 4/2004 | Karason et al. |
| 2004/0122434 A1 | 6/2004 | Argenta et al. |
| 2004/0126413 A1 | 7/2004 | Sigurjonsson et al. |
| 2004/0127862 A1 | 7/2004 | Bubb et al. |
| 2004/0127863 A1 | 7/2004 | Bubb et al. |
| 2004/0167482 A1 | 8/2004 | Watson |
| 2004/0167617 A1 | 8/2004 | Voellmicke et al. |
| 2004/0171976 A1 | 9/2004 | Johnson |
| 2004/0171998 A1 | 9/2004 | Marasco, Jr. |
| 2004/0241214 A1 | 12/2004 | Kirkwood et al. |
| 2004/0249353 A1 | 12/2004 | Risks, Jr. et al. |
| 2005/0013957 A1 | 1/2005 | Leschinsky |
| 2005/0020955 A1 | 1/2005 | Sanders et al. |
| 2005/0058694 A1 * | 3/2005 | Nielsen .................. A61L 15/60 424/445 |
| 2005/0070835 A1 * | 3/2005 | Joshi ..................... A61M 1/962 602/41 |
| 2005/0085768 A1 | 4/2005 | Greter et al. |
| 2005/0090787 A1 | 4/2005 | Risk, Jr. et al. |
| 2005/0131327 A1 | 6/2005 | Lockwood et al. |
| 2005/0148913 A1 * | 7/2005 | Weston .................. A61M 1/964 602/2 |
| 2005/0165350 A1 | 7/2005 | Greter et al. |
| 2005/0222544 A1 * | 10/2005 | Weston ................... A61M 1/60 604/315 |
| 2005/0228329 A1 | 10/2005 | Boehringer et al. |
| 2005/0230422 A1 | 10/2005 | Muller et al. |
| 2005/0245850 A1 | 11/2005 | Freyre et al. |
| 2005/0261642 A1 * | 11/2005 | Weston .................... A61M 1/98 604/313 |
| 2005/0283105 A1 | 12/2005 | Heaton et al. |
| 2006/0009744 A1 | 1/2006 | Erdman et al. |
| 2006/0029650 A1 * | 2/2006 | Coffey .................... A61L 15/32 424/443 |
| 2006/0069365 A1 * | 3/2006 | Sperl ..................... A61F 13/539 604/368 |
| 2006/0070458 A1 | 4/2006 | Jones et al. |
| 2006/0079599 A1 | 4/2006 | Arthur |
| 2006/0100586 A1 | 5/2006 | Karpowicz et al. |
| 2006/0149170 A1 | 7/2006 | Boynton et al. |
| 2006/0155260 A1 * | 7/2006 | Blott .................... A61M 3/0208 604/543 |
| 2006/0173514 A1 | 8/2006 | Biel et al. |
| 2006/0253082 A1 | 11/2006 | McIntosh et al. |
| 2006/0273109 A1 | 12/2006 | Keller |
| 2006/0282028 A1 | 12/2006 | Howard et al. |
| 2007/0004896 A1 | 1/2007 | Ito et al. |

(56) References Cited

U.S. PATENT DOCUMENTS

| | | |
|---|---|---|
| 2007/0005028 A1 | 1/2007 | Risk, Jr. et al. |
| 2007/0009580 A1 | 1/2007 | DiCosmo et al. |
| 2007/0021697 A1 | 1/2007 | Ginther et al. |
| 2007/0032762 A1 | 2/2007 | Vogel |
| 2007/0032778 A1 | 2/2007 | Heaton et al. |
| 2007/0038172 A1 | 2/2007 | Zamierowski |
| 2007/0040454 A1 | 2/2007 | Freudenberger et al. |
| 2007/0055209 A1 | 3/2007 | Patel et al. |
| 2007/0141101 A1 | 6/2007 | Nugent et al. |
| 2007/0147947 A1 | 6/2007 | Stenton et al. |
| 2007/0164047 A1 | 7/2007 | Reidt et al. |
| 2007/0167884 A1 | 7/2007 | Mangrum et al. |
| 2007/0179460 A1 | 8/2007 | Adahan |
| 2007/0185463 A1 | 8/2007 | Mulligan |
| 2007/0203062 A1 | 8/2007 | Ellis-Behnke et al. |
| 2007/0219513 A1 | 9/2007 | Lina et al. |
| 2007/0219532 A1 | 9/2007 | Karpowicz et al. |
| 2007/0225663 A1 | 9/2007 | Watt et al. |
| 2007/0255194 A1* | 11/2007 | Gudnason ........... A61F 13/0203 602/900 |
| 2007/0260207 A1 | 11/2007 | Ugander et al. |
| 2007/0276195 A1 | 11/2007 | Xu et al. |
| 2007/0276309 A1 | 11/2007 | Xu et al. |
| 2008/0004549 A1 | 1/2008 | Anderson et al. |
| 2008/0009812 A1 | 1/2008 | Riesinger |
| 2008/0031748 A1 | 2/2008 | Ihle et al. |
| 2008/0033352 A1 | 2/2008 | Annis et al. |
| 2008/0039761 A1 | 2/2008 | Heaton et al. |
| 2008/0045887 A1 | 2/2008 | Larsson et al. |
| 2008/0060550 A1 | 3/2008 | MacDonald et al. |
| 2008/0071216 A1 | 3/2008 | Locke et al. |
| 2008/0089173 A1 | 4/2008 | Lu et al. |
| 2008/0132821 A1 | 6/2008 | Propp et al. |
| 2008/0188820 A1 | 8/2008 | Joshi |
| 2008/0200905 A1 | 8/2008 | Heaton et al. |
| 2008/0206155 A1 | 8/2008 | Tamarkin et al. |
| 2008/0208147 A1 | 8/2008 | Argenta et al. |
| 2008/0208163 A1 | 8/2008 | Wilkie |
| 2008/0223378 A1 | 9/2008 | Henderson et al. |
| 2008/0234641 A1 | 9/2008 | Locke et al. |
| 2008/0254103 A1 | 10/2008 | Harris et al. |
| 2008/0287880 A1 | 11/2008 | Keller |
| 2008/0294147 A1 | 11/2008 | Radl et al. |
| 2008/0300555 A1 | 12/2008 | Olson et al. |
| 2008/0306407 A1 | 12/2008 | Taylor |
| 2008/0306456 A1 | 12/2008 | Riesinger |
| 2008/0312572 A1 | 12/2008 | Riesinger |
| 2008/0312613 A1 | 12/2008 | Heaton et al. |
| 2008/0314929 A1 | 12/2008 | Keller |
| 2009/0005746 A1 | 1/2009 | Nielsen et al. |
| 2009/0020561 A1 | 1/2009 | Keller |
| 2009/0022779 A1 | 1/2009 | Kelly et al. |
| 2009/0030086 A1 | 1/2009 | Eady et al. |
| 2009/0036873 A1 | 2/2009 | Nielsen et al. |
| 2009/0054855 A1 | 2/2009 | Blott et al. |
| 2009/0054856 A1 | 2/2009 | Mormino et al. |
| 2009/0082740 A1 | 3/2009 | Lockwood et al. |
| 2009/0093550 A1 | 4/2009 | Rolfes et al. |
| 2009/0093779 A1 | 4/2009 | Riesinger |
| 2009/0098073 A1 | 4/2009 | MacDonald et al. |
| 2009/0125004 A1 | 5/2009 | Shen et al. |
| 2009/0131888 A1 | 5/2009 | Joshi |
| 2009/0131892 A1 | 5/2009 | Karpowicz et al. |
| 2009/0134186 A1 | 5/2009 | Keller |
| 2009/0137973 A1 | 5/2009 | Karpowicz et al. |
| 2009/0157017 A1 | 6/2009 | Ambrosio |
| 2009/0157024 A1 | 6/2009 | Song |
| 2009/0192467 A1 | 7/2009 | Hansen et al. |
| 2009/0196844 A1 | 8/2009 | Choi et al. |
| 2009/0198201 A1 | 8/2009 | Adahan |
| 2009/0204085 A1 | 8/2009 | Biggie et al. |
| 2009/0216170 A1 | 8/2009 | Robinson et al. |
| 2009/0216204 A1 | 8/2009 | Bhavaraju et al. |
| 2009/0221977 A1 | 9/2009 | Blott et al. |
| 2009/0234306 A1 | 9/2009 | Vitaris |
| 2009/0240218 A1 | 9/2009 | Braga et al. |
| 2009/0254053 A1 | 10/2009 | Svensby et al. |
| 2009/0254066 A1 | 10/2009 | Heaton et al. |
| 2009/0259203 A1 | 10/2009 | Hu et al. |
| 2009/0264807 A1 | 10/2009 | Haggstrom et al. |
| 2009/0270820 A1 | 10/2009 | Johnson et al. |
| 2009/0275872 A1 | 11/2009 | Addison et al. |
| 2009/0275922 A1 | 11/2009 | Coulthard et al. |
| 2009/0287129 A1 | 11/2009 | Boehringer et al. |
| 2009/0293887 A1 | 12/2009 | Wilkes et al. |
| 2009/0299251 A1 | 12/2009 | Buan |
| 2009/0299255 A1 | 12/2009 | Kazala, Jr. et al. |
| 2009/0299257 A1 | 12/2009 | Long et al. |
| 2009/0299306 A1 | 12/2009 | Buan |
| 2009/0312723 A1 | 12/2009 | Blott et al. |
| 2010/0004611 A1 | 1/2010 | Aali |
| 2010/0016767 A1 | 1/2010 | Jones et al. |
| 2010/0022972 A1 | 1/2010 | Lina et al. |
| 2010/0030170 A1 | 2/2010 | Keller et al. |
| 2010/0030171 A1 | 2/2010 | Canada et al. |
| 2010/0030178 A1 | 2/2010 | MacMeccan et al. |
| 2010/0036305 A1 | 2/2010 | Green |
| 2010/0036334 A1 | 2/2010 | Heagle et al. |
| 2010/0036367 A1 | 2/2010 | Krohn |
| 2010/0069829 A1 | 3/2010 | Hutchinson et al. |
| 2010/0069850 A1 | 3/2010 | Fabo |
| 2010/0069858 A1 | 3/2010 | Olson |
| 2010/0069863 A1 | 3/2010 | Olson |
| 2010/0087767 A1* | 4/2010 | McNeil ............ A61F 13/00068 602/42 |
| 2010/0094234 A1 | 4/2010 | Ramella et al. |
| 2010/0106112 A1 | 4/2010 | Vogel |
| 2010/0106117 A1 | 4/2010 | Lockwood et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0145289 A1 | 6/2010 | Lina et al. |
| 2010/0159192 A1 | 6/2010 | Cotton |
| 2010/0160878 A1 | 6/2010 | Hunt et al. |
| 2010/0160879 A1* | 6/2010 | Weston ................. A61M 1/985 604/319 |
| 2010/0160880 A1* | 6/2010 | Weston .................. A61M 1/80 604/319 |
| 2010/0168633 A1 | 7/2010 | Bougherara et al. |
| 2010/0174251 A1* | 7/2010 | Weston .................. A61M 1/74 604/320 |
| 2010/0210986 A1 | 8/2010 | Sanders et al. |
| 2010/0230467 A1 | 9/2010 | Criscuolo et al. |
| 2010/0249733 A9 | 9/2010 | Blott et al. |
| 2010/0262090 A1 | 10/2010 | Riesinger |
| 2010/0262091 A1 | 10/2010 | Larsson |
| 2010/0268176 A1 | 10/2010 | Johnson et al. |
| 2010/0280468 A1 | 11/2010 | Haggstrom et al. |
| 2010/0286639 A1* | 11/2010 | Scholz ................ A61F 13/0246 602/54 |
| 2010/0305490 A1 | 12/2010 | Coulthard et al. |
| 2010/0318052 A1* | 12/2010 | Ha ...................... A61F 13/0226 604/385.01 |
| 2011/0004172 A1 | 1/2011 | Eckstein et al. |
| 2011/0004173 A1 | 1/2011 | Hu et al. |
| 2011/0009838 A1* | 1/2011 | Greener ............ A61F 13/0226 604/319 |
| 2011/0021431 A1 | 1/2011 | Jones et al. |
| 2011/0022013 A1 | 1/2011 | Boynton et al. |
| 2011/0028919 A1 | 2/2011 | Johnnison et al. |
| 2011/0028920 A1 | 2/2011 | Johannison |
| 2011/0028921 A1 | 2/2011 | Hartwell et al. |
| 2011/0033503 A1 | 2/2011 | Sinko et al. |
| 2011/0034869 A1 | 2/2011 | Greter et al. |
| 2011/0034888 A1 | 2/2011 | Aali |
| 2011/0034894 A1 | 2/2011 | Riesinger |
| 2011/0046585 A1* | 2/2011 | Weston ................. A61M 1/966 604/320 |
| 2011/0054421 A1* | 3/2011 | Hartwell ............ A61F 13/0216 604/319 |
| 2011/0054423 A1 | 3/2011 | Blott et al. |
| 2011/0086077 A1 | 4/2011 | McCrea et al. |

(56) References Cited

U.S. PATENT DOCUMENTS

| | | | |
|---|---|---|---|
| 2011/0087178 A2* | 4/2011 | Weston | A61M 1/98 604/319 |
| 2011/0092958 A1 | 4/2011 | Jacobs | |
| 2011/0105963 A1 | 5/2011 | Hu et al. | |
| 2011/0106030 A1 | 5/2011 | Scholz | |
| 2011/0112492 A1 | 5/2011 | Bharti et al. | |
| 2011/0118683 A1* | 5/2011 | Weston | A61M 1/732 604/319 |
| 2011/0125066 A1 | 5/2011 | Robinson et al. | |
| 2011/0130712 A1 | 6/2011 | Topaz | |
| 2011/0172615 A2* | 7/2011 | Greener | A61F 13/0226 604/319 |
| 2011/0172617 A1 | 7/2011 | Riesinger | |
| 2011/0270201 A1 | 11/2011 | Bubb et al. | |
| 2011/0270202 A1 | 11/2011 | Boehringer et al. | |
| 2011/0295220 A1 | 12/2011 | Heaton et al. | |
| 2011/0313373 A1 | 12/2011 | Riesinger | |
| 2011/0313374 A1 | 12/2011 | Lockwood et al. | |
| 2012/0053538 A1 | 3/2012 | Blott et al. | |
| 2012/0109085 A1 | 5/2012 | McNeil | |
| 2012/0130332 A1 | 5/2012 | Cotton et al. | |
| 2013/0066285 A1 | 3/2013 | Locke et al. | |
| 2013/0090615 A1 | 4/2013 | Jaeb et al. | |
| 2013/0102979 A1 | 4/2013 | Coulthard et al. | |
| 2013/0138054 A1 | 5/2013 | Fleischmann | |
| 2013/0144230 A1 | 6/2013 | Wu et al. | |
| 2013/0150814 A1 | 6/2013 | Buan | |
| 2013/0165878 A1 | 6/2013 | Heagle | |
| 2013/0274688 A1 | 10/2013 | Weston | |
| 2013/0331822 A1 | 12/2013 | Patel et al. | |
| 2013/0338614 A1 | 12/2013 | Heaton et al. | |
| 2014/0039423 A1 | 2/2014 | Riesinger | |
| 2014/0114268 A1 | 4/2014 | Auguste et al. | |
| 2014/0155849 A1 | 6/2014 | Heaton et al. | |
| 2014/0228791 A1 | 8/2014 | Hartwell | |
| 2014/0236109 A1* | 8/2014 | Greener | A61F 13/0226 604/319 |
| 2014/0343519 A1* | 11/2014 | Weston | A61F 13/0216 604/319 |
| 2015/0032035 A1 | 1/2015 | Banwell et al. | |
| 2015/0065965 A1 | 3/2015 | Haggstrom et al. | |
| 2015/0174304 A1 | 6/2015 | Askem et al. | |
| 2015/0190286 A1 | 7/2015 | Allen et al. | |
| 2015/0209492 A1 | 7/2015 | Blott et al. | |
| 2015/0216733 A1 | 8/2015 | Allen et al. | |
| 2015/0308994 A1 | 10/2015 | Hammond et al. | |
| 2016/0038345 A1* | 2/2016 | Ha | A61F 13/0226 602/54 |
| 2016/0051737 A1 | 2/2016 | Joshi et al. | |
| 2016/0081859 A1 | 3/2016 | Hartwell | |
| 2016/0256613 A1* | 9/2016 | Weston | A61M 1/74 |
| 2016/0317357 A1 | 11/2016 | Vitaris et al. | |
| 2017/0095598 A1 | 4/2017 | Joshi et al. | |
| 2017/0128642 A1 | 5/2017 | Buan | |
| 2017/0181896 A1 | 6/2017 | Hartwell | |
| 2017/0181897 A1 | 6/2017 | Hartwell | |
| 2017/0258973 A1* | 9/2017 | Weston | A61F 13/0216 |
| 2018/0361039 A1* | 12/2018 | Greener | A61M 1/915 |
| 2019/0314209 A1* | 10/2019 | Ha | A61F 13/0233 |
| 2020/0143003 A1* | 5/2020 | Klein | G06F 30/13 |
| 2021/0228417 A1* | 7/2021 | Ha | A61F 13/00059 |
| 2021/0322666 A1* | 10/2021 | Greener | A61M 1/964 |
| 2023/0338196 A1* | 10/2023 | Greener | A61F 13/0226 |

FOREIGN PATENT DOCUMENTS

| | | |
|---|---|---|
| CA | 2390513 A1 | 5/2001 |
| CA | 2121688 C | 7/2001 |
| CA | 2408305 A1 | 11/2001 |
| CA | 2458285 A1 | 3/2003 |
| CA | 2157772 C | 9/2003 |
| CN | 2186074 Y | 12/1994 |
| DE | 847475 C | 8/1952 |
| DE | 2809828 A1 | 9/1978 |
| DE | 3137839 A1 | 3/1983 |
| DE | 3032092 C2 | 10/1984 |
| DE | 3443101 A1 | 5/1986 |
| DE | 3935818 A1 | 5/1991 |
| DE | 4012232 A1 | 10/1991 |
| DE | 9017289 U1 | 4/1992 |
| DE | 19844355 A1 | 4/2000 |
| DE | 202004017052 U1 | 6/2005 |
| EP | 0020662 B1 | 7/1984 |
| EP | 0257916 A1 | 3/1988 |
| EP | 0340018 A2 | 11/1989 |
| EP | 0353972 A1 | 2/1990 |
| EP | 0355186 A1 | 2/1990 |
| EP | 0521434 A1 | 1/1993 |
| EP | 0541251 A1 | 5/1993 |
| EP | 0619105 A1 | 10/1994 |
| EP | 0858810 A2 | 8/1998 |
| EP | 0777504 B1 | 10/1998 |
| EP | 0888141 A1 | 1/1999 |
| EP | 0782421 B1 | 7/1999 |
| EP | 1007015 A1 | 6/2000 |
| EP | 1013290 A1 | 6/2000 |
| EP | 1029585 A1 | 8/2000 |
| EP | 1105171 A2 | 6/2001 |
| EP | 1105180 A1 | 6/2001 |
| EP | 1107813 A1 | 6/2001 |
| EP | 1030657 B1 | 10/2001 |
| EP | 0708620 B1 | 5/2003 |
| EP | 1306123 A1 | 5/2003 |
| EP | 1088569 B1 | 8/2003 |
| EP | 1411874 A1 | 4/2004 |
| EP | 1440737 A1 | 7/2004 |
| EP | 1452156 A1 | 9/2004 |
| EP | 1440667 B1 | 3/2006 |
| EP | 1284777 B1 | 4/2006 |
| EP | 1263366 B1 | 7/2006 |
| EP | 1726276 A2 | 11/2006 |
| EP | 1171065 B1 | 3/2007 |
| EP | 1880840 A1 | 1/2008 |
| EP | 1476217 B1 | 3/2008 |
| EP | 1897569 A1 | 3/2008 |
| EP | 1923077 A1 | 5/2008 |
| EP | 1955887 A2 | 8/2008 |
| EP | 1985270 A2 | 10/2008 |
| EP | 1121163 B1 | 11/2008 |
| EP | 2079507 A2 | 7/2009 |
| EP | 2098257 A1 | 9/2009 |
| EP | 2111804 A2 | 10/2009 |
| EP | 2161011 A1 | 3/2010 |
| EP | 2185206 A2 | 5/2010 |
| EP | 1718257 B1 | 8/2010 |
| EP | 2218431 A2 | 8/2010 |
| EP | 2326295 A1 | 6/2011 |
| EP | 2335749 A1 | 6/2011 |
| EP | 2349155 A2 | 8/2011 |
| EP | 2420214 A1 | 2/2012 |
| EP | 2021046 B1 | 3/2012 |
| EP | 2178573 B1 | 6/2012 |
| EP | 2462908 A1 | 6/2012 |
| EP | 2711034 A1 | 3/2014 |
| EP | 2305325 B1 | 4/2014 |
| EP | 2345437 B1 | 4/2014 |
| EP | 2648668 A4 | 1/2015 |
| EP | 2687245 B1 | 2/2016 |
| FR | 1163907 A | 10/1958 |
| GB | 114754 A | 4/1918 |
| GB | 236350 A | 7/1925 |
| GB | 641061 A | 8/1950 |
| GB | 1224009 A | 3/1971 |
| GB | 1255395 A | 12/1971 |
| GB | 1400124 A | 7/1975 |
| GB | 1549756 A | 8/1979 |
| GB | 2099306 A | 12/1982 |
| GB | 2061732 B | 6/1983 |
| GB | 2195255 A | 4/1988 |
| GB | 2288734 A | 11/1995 |
| GB | 2307180 A | 5/1997 |
| GB | 2378392 A | 2/2003 |
| GB | 2415908 A | 1/2006 |

(56) References Cited

FOREIGN PATENT DOCUMENTS

| | | |
|---|---|---|
| GB | 2424582 A | 10/2006 |
| GB | 2435419 A | 8/2007 |
| GB | 2435422 A | 8/2007 |
| GB | 0722820 | 7/2019 |
| JP | S5986824 U | 6/1984 |
| JP | S5987824 U | 6/1984 |
| JP | S6180018 A | 4/1986 |
| JP | S6180018 U | 5/1986 |
| JP | 2003165843 A | 6/2003 |
| JP | 2005334188 A | 12/2005 |
| SU | 1251912 A1 | 8/1986 |
| WO | WO-8300742 A1 | 3/1983 |
| WO | WO-8401904 A1 | 5/1984 |
| WO | WO-9011795 A1 | 10/1990 |
| WO | WO-9100718 A1 | 1/1991 |
| WO | WO-9209301 A1 | 6/1992 |
| WO | WO-9209651 A1 | 6/1992 |
| WO | WO-9216245 A1 | 10/1992 |
| WO | WO-9220299 A2 | 11/1992 |
| WO | WO-9306802 A1 | 4/1993 |
| WO | WO-9309176 A2 | 5/1993 |
| WO | WO-9420041 A1 | 9/1994 |
| WO | WO-9420133 A1 | 9/1994 |
| WO | WO-9423677 A2 | 10/1994 |
| WO | WO-9504511 A1 | 2/1995 |
| WO | WO-9514451 A1 | 6/1995 |
| WO | WO-9529959 A1 | 11/1995 |
| WO | WO-9605873 A1 | 2/1996 |
| WO | WO-9621410 A1 | 7/1996 |
| WO | WO-9640174 A1 | 12/1996 |
| WO | WO-9703717 A1 | 2/1997 |
| WO | WO-9711658 A1 | 4/1997 |
| WO | WO-9733922 A1 | 9/1997 |
| WO | WO-9742986 A1 | 11/1997 |
| WO | WO-9803267 A1 | 1/1998 |
| WO | WO-9806444 A1 | 2/1998 |
| WO | WO-9901173 A1 | 1/1999 |
| WO | WO-9917698 A1 | 4/1999 |
| WO | WO-9930629 A1 | 6/1999 |
| WO | WO-9939671 A1 | 8/1999 |
| WO | WO-9947097 A2 | 9/1999 |
| WO | WO-9965536 A1 | 12/1999 |
| WO | WO-0007653 A1 | 2/2000 |
| WO | WO-0038752 A1 | 7/2000 |
| WO | WO-0042957 A1 | 7/2000 |
| WO | WO-0050143 A1 | 8/2000 |
| WO | WO-0059424 A1 | 10/2000 |
| WO | WO-0061206 A1 | 10/2000 |
| WO | WO-0062827 A2 | 10/2000 |
| WO | WO-0064396 A1 | 11/2000 |
| WO | WO-0119430 A1 | 3/2001 |
| WO | WO-0134223 A1 | 5/2001 |
| WO | WO-0137922 A2 | 5/2001 |
| WO | WO-0162312 A1 | 8/2001 |
| WO | WO-0166017 A1 | 9/2001 |
| WO | WO-0185248 A1 | 11/2001 |
| WO | WO-0193793 A1 | 12/2001 |
| WO | WO-0202079 A1 | 1/2002 |
| WO | WO-0217840 A1 | 3/2002 |
| WO | WO-0226180 A1 | 4/2002 |
| WO | WO-0238096 A2 | 5/2002 |
| WO | WO-02070040 A1 | 9/2002 |
| WO | WO-02076379 A2 | 10/2002 |
| WO | WO-02083046 A1 | 10/2002 |
| WO | WO-02092783 A2 | 11/2002 |
| WO | WO-02094256 A1 | 11/2002 |
| WO | WO-02102864 A1 | 12/2002 |
| WO | WO-03045492 A1 | 6/2003 |
| WO | WO-03057307 A1 | 7/2003 |
| WO | WO-03074100 A1 | 9/2003 |
| WO | WO-03092620 A2 | 11/2003 |
| WO | WO-2004024300 A1 | 3/2004 |
| WO | WO-2004037334 A1 | 5/2004 |
| WO | WO-2004054632 A1 | 7/2004 |
| WO | WO-2004073566 A1 | 9/2004 |
| WO | WO-2004077387 A1 | 9/2004 |
| WO | WO-2005009488 A2 | 2/2005 |
| WO | WO-2005016179 A2 | 2/2005 |
| WO | WO-2005017000 A1 | 2/2005 |
| WO | WO-2005018695 A1 | 3/2005 |
| WO | WO-2005025447 A2 | 3/2005 |
| WO | WO-2005025666 A2 | 3/2005 |
| WO | WO-2005046761 A1 | 5/2005 |
| WO | WO-2005051461 A1 | 6/2005 |
| WO | WO-2005070480 A1 | 8/2005 |
| WO | WO-2005079718 A1 | 9/2005 |
| WO | WO-2005082435 A1 | 9/2005 |
| WO | WO-2005105180 A1 | 11/2005 |
| WO | WO-2005118011 A1 | 12/2005 |
| WO | WO-2005123170 A1 | 12/2005 |
| WO | WO-2006014534 A2 | 2/2006 |
| WO | WO-2006030054 A1 | 3/2006 |
| WO | WO-2006034128 A2 | 3/2006 |
| WO | WO-2006048246 A1 | 5/2006 |
| WO | WO-2006052745 A2 | 5/2006 |
| WO | WO-2006052839 A2 | 5/2006 |
| WO | WO-2006056294 A1 | 6/2006 |
| WO | WO-2006081403 A1 | 8/2006 |
| WO | WO-2006116992 A1 | 11/2006 |
| WO | WO-2006135506 A2 | 12/2006 |
| WO | WO-2007002835 A2 | 1/2007 |
| WO | WO-2007013064 A1 | 2/2007 |
| WO | WO-2007019038 A2 | 2/2007 |
| WO | WO-2007024230 A1 | 3/2007 |
| WO | WO-2007030598 A2 | 3/2007 |
| WO | WO-2007030599 A2 | 3/2007 |
| WO | WO-2007030601 A2 | 3/2007 |
| WO | WO-2007084792 A2 | 7/2007 |
| WO | WO-2007085396 A1 | 8/2007 |
| WO | WO-2007092405 A2 | 8/2007 |
| WO | WO-2007106592 A2 | 9/2007 |
| WO | WO-2007106594 A2 | 9/2007 |
| WO | WO-2007124198 A2 | 11/2007 |
| WO | WO-2007133618 A2 | 11/2007 |
| WO | WO-2008013896 A2 | 1/2008 |
| WO | WO-2008027449 A2 | 3/2008 |
| WO | WO-2008036345 A1 | 3/2008 |
| WO | WO-2008039223 A1 | 4/2008 |
| WO | WO-2008040020 A2 | 4/2008 |
| WO | WO-2008041926 A1 | 4/2008 |
| WO | WO-2008049277 A1 | 5/2008 |
| WO | WO-2008076407 A2 | 6/2008 |
| WO | WO-2008082444 A2 | 7/2008 |
| WO | WO-2008100437 A1 | 8/2008 |
| WO | WO-2008100440 A1 | 8/2008 |
| WO | WO-2008112304 A1 | 9/2008 |
| WO | WO-2008131895 A1 | 11/2008 |
| WO | WO-2008131985 A1 | 11/2008 |
| WO | WO-2008134544 A1 | 11/2008 |
| WO | WO-2008134774 A2 | 11/2008 |
| WO | WO-2008141228 A1 | 11/2008 |
| WO | WO-2008141470 A1 | 11/2008 |
| WO | WO-2009019227 A2 | 2/2009 |
| WO | WO-2009019229 A2 | 2/2009 |
| WO | WO-2009034322 A2 | 3/2009 |
| WO | WO-2009042514 A1 | 4/2009 |
| WO | WO-2009047524 A1 | 4/2009 |
| WO | WO-2009052193 A1 | 4/2009 |
| WO | WO-2009060327 A2 | 5/2009 |
| WO | WO-2009062327 A1 | 5/2009 |
| WO | WO-2009066104 A1 | 5/2009 |
| WO | WO-2009066105 A1 | 5/2009 |
| WO | WO-2009066106 A1 | 5/2009 |
| WO | WO-2009070905 A1 | 6/2009 |
| WO | WO-2009078790 A1 | 6/2009 |
| WO | WO-2009089390 A2 | 7/2009 |
| WO | WO-2009103031 A1 | 8/2009 |
| WO | WO-2009111657 A2 | 9/2009 |
| WO | WO-2009117635 A1 | 9/2009 |
| WO | WO-2009122989 A1 | 10/2009 |
| WO | WO-2009124100 A1 | 10/2009 |
| WO | WO-2009126833 A2 | 10/2009 |
| WO | WO-2009145703 A1 | 12/2009 |
| WO | WO-2009146441 A1 | 12/2009 |

(56) References Cited

FOREIGN PATENT DOCUMENTS

| | | |
|---|---|---|
| WO | WO-2009147402 A2 | 12/2009 |
| WO | WO-2009151380 A1 | 12/2009 |
| WO | WO-2009156709 A1 | 12/2009 |
| WO | WO-2009158124 A1 | 12/2009 |
| WO | WO-2009158128 A2 | 12/2009 |
| WO | WO-2009158130 A1 | 12/2009 |
| WO | WO-2010026251 A1 | 3/2010 |
| WO | WO-2010033271 A1 | 3/2010 |
| WO | WO-2010042240 A1 | 4/2010 |
| WO | WO-2010051068 A1 | 5/2010 |
| WO | WO-2010051418 A2 | 5/2010 |
| WO | WO-2010059849 A2 | 5/2010 |
| WO | WO-2010072309 A1 | 7/2010 |
| WO | WO-2010072395 A1 | 7/2010 |
| WO | WO-2010082872 A1 | 7/2010 |
| WO | WO-2010089448 A1 | 8/2010 |
| WO | WO-2010120776 A1 | 10/2010 |
| WO | WO-2010139926 A1 | 12/2010 |
| WO | WO-2010141271 A1 | 12/2010 |
| WO | WO-2010142959 A2 | 12/2010 |
| WO | WO-2010147592 A1 | 12/2010 |
| WO | WO-2011019476 A1 | 2/2011 |
| WO | WO-2011023275 A1 | 3/2011 |
| WO | WO-2011023650 A1 | 3/2011 |
| WO | WO-2011128651 A1 | 10/2011 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO-2012009370 A2 | 1/2012 |
| WO | WO-2012022484 A1 | 2/2012 |
| WO | WO-2012074512 A1 | 6/2012 |
| WO | WO-2012131237 A1 | 10/2012 |
| WO | WO-2012140378 A1 | 10/2012 |
| WO | WO-2012143665 A1 | 10/2012 |
| WO | WO-2012146656 A1 | 11/2012 |
| WO | WO-2012150235 A1 | 11/2012 |
| WO | WO-2012151359 A1 | 11/2012 |
| WO | WO-2013010907 A1 | 1/2013 |
| WO | WO-2013083800 A1 | 6/2013 |
| WO | WO-2013090810 A1 | 6/2013 |
| WO | WO-2013149078 A1 | 10/2013 |
| WO | WO-2014008348 A2 | 1/2014 |
| WO | WO-2014016759 A1 | 1/2014 |
| WO | WO-2014108476 A1 | 7/2014 |
| WO | WO-2014113253 A1 | 7/2014 |
| WO | WO-2015022334 A1 | 2/2015 |
| WO | WO-2015022340 A1 | 2/2015 |

OTHER PUBLICATIONS

US 6,306,115 B1, 10/2001, Kelly et al. (withdrawn)

3M Tegaderm, "Transparent Film Dressings," Product Profile, filed in Opposition Proceedings for European Patent No. 2214610, mailed on Aug. 4, 2020, 8 pages.

Achterberg V., et al., "Hydroactive Dressings and Serum Proteins: An In Vitro Study," Journal of Wound Care, vol. 5 (2), Feb. 1996, pp. 79-82.

Advantec MFS, Inc., "Membrane Filters" (catalog), retrieved from http://www.advantecmfs.com/catalog/filt/membrane.pdf, on Jan. 29, 2016, Copyright 2001-2011, 17 pages.

Annex to the Communication, re the Opposition of European Patent No. EP2214610, dated Mar. 3, 2020, 17 pages.

Argenta L C., et al., "Vacuum-Assisted Closure: A New Method for Wound Control and Treatment: Clinical Experience," Annals of Plastic Surgery, vol. 38 (6), Jun. 1997, pp. 563-577.

Arnljots B., et al., "Irrigation Treatment in Split-Thickness Skin Grafting of Intractable Leg Ulcers," Scandinavian Journal of Plastic and Reconstructive Surgery, vol. 19, 1985, pp. 211-213.

Aubrey D.A., et al., "Treatment of the Perineal Wound after Proctectomy by Intermittent Irrigation," Arch. Surg, vol. 119, Oct. 1984, pp. 1141-1144.

Bagautdinov N.A., "Variant of External Vacuum Aspiration in the Treatment of Purulent Diseases of Soft Tissues," in Current Problems in Modern Clinical Surgery, Interdepartmental Collection, 1986, pp. 94-96.

Basf, Elastollan Physical Properties, 2020, 1 page.

Bevan D., et al., "Diverse and potent activities of HGF/SF in skin wound repair," Journal of Pathology, vol. 203, 2004, pp. 831-838.

Biblehimer H.L., "Dealing With a Wound that Drains 1.5 Liters a Day," RN, Aug. 1986, pp. 21-23.

Bier A., "Hyperemia as a Therapeutic Agent," UCI CCM Library, 1905, pp. 74-85.

Bragina, I.O., et al., "Radical Phenylation of Amides of Thiocinnamic Acid," Russian Chemical Bulletin, Dec. 31, 1983, 3 pages.

Brief Communication on Oral proceedings—Letter from the Opponent, re the Opposition of European Patent No. EP2214610, dated Feb. 26, 2021, 6 pages.

Brubacher L.L., "To Heal a Draining Wound," RN, Mar. 1982, pp. 30-35.

Bucalo B., et al., "Inhibition of Cell Proliferation by Chronic Wound Fluid," Wound Repair and Regeneration, Miami, Jul.-Sep. 1993, pp. 181-186.

Chariker M.E., et al., "Effective Management of Incisional and Cutaneous Fistulae with Closed Suction Wound Drainage," Contemporary Surgery, vol. 34, Jun. 1989, pp. 59-63.

Chintamani et al., "Half Versus Full Vacuum Suction Drainage After Modified Radical Mastectomy for Breast Cancer—a Prospective Randomized Clinical Trial," BMC Cancer, Research Article, vol. 5(11), Jan. 27, 2005, 5 pages.

Costunchenok B M., et al., "Effect of Vacuum on Surgical Purulent Wounds," Vestnik Chirurgia, Sep. 1986, 6 pages.

Davydov Y A., et al., "Concepts for Clinical Biological Management of the Wound Process in the Treatment of Purulent Wounds Using Vacuum Therapy," Vestnik Khirurgii, Feb. 1991, pp. 15-17.

Davydov Y.A., et al., "Pathogenic Mechanisms of the Effect of Vacuum Therapy on the Course of the Wound Process," Khirurgiya, vol. 6, Dec. 1990, pp. 42-47.

Davydov Y.A., et al., "The Bacteriological and Cytological Assessment of Vacuum Therapy of Purulent Wounds," Vestnik Khirurgii, Oct. 1988, pp. 11-14.

Davydov Y.A., et al., "Vacuum Therapy in the Treatment of Purulent Lactation Mastitis," The Kremlin Papers: Perspectives in Wound Care, Vestnik Khirurgii, BlueSky Publishing, 2004, pp. 5-7.

De Lange M.Y., et al., "Vacuum-Assisted Closure: Indications and Clinical Experience," Eur J Plast Surg (2000), vol. 23, Feb. 9, 2000, pp. 178-182.

Decision revoking the European Patent (Art. 101 (3)(b) EPC) for European Patent No. 2214610, mailed on Nov. 15, 2021, 43 pages.

Dilmaghani A., et al., "A Method for Closed Irrigation and Suction Therapy in Deep Wound Infections," Journal of Bone and Joint Surgery, Mar. 1969, vol. 51-A(2), pp. 323-342.

Fleischmann W., et al., "Vacuum Sealing: Indication, Technique, And Results," Eur J Orthop Surg Traumatol, vol. 5, 1995, pp. 37-40.

Fleischmann W., "Vakuumversiegelung zur Behandlung von Problemwunden" Wund Forum Spezial, (with English translation: Vacuum Sealing for Treatment of Problematical Wounds), IHW '94, pp. 54-55 (6 pages with English translation).

Forwarding of submissions to parties of a letter of the Opponent for European Patent No. 2214610, dated Jul. 19, 2022, 12 pages.

Garcia-Rinaldi R., et al., "Improving the Efficiency of Wound Drainage Catheters," American Journal of Surgery, Sep. 1975, vol. 130, pp. 372-373.

Greer S.E., et al., "Techniques for Applying Subatmospheric Pressure Dressing to Wounds in Difficult Regions of Anatomy," JWOCN, vol. 26(5), Sep. 1999, pp. 250-253.

Hartz R.S., et al., "Healing of the Perineal Wound," The Archives of Surgery, Apr. 1980, vol. 115, pp. 471-474.

Health Technology Literature Review, "Vacuum Assisted Closure Therapy for Wound Care," The Medical Advisory Secretariat, Dec. 2004, pp. 1-57.

Hersle K., et al., "Uses of Dextranomer Absorbent Pads After Cryosurgery of Cutaneous Malignancies," The Journal of Dermatologic Surgery and Oncology, vol. 8, Jan. 1982, pp. 35-37.

Info V.A.C. User Manual, KCI on Dec. 1, 2006 in 76 pages.

(56) References Cited

OTHER PUBLICATIONS

Information about the Result of Oral Proceedings, the Opposition of European Patent No. 2214610, dated Oct. 8, 2021, 7 pages.
International Preliminary Report on Patentability for Application No. PCT/GB2008/051088, dated May 25, 2010, 7 pages.
International Search Report for Application No. PCT/GB2008/051088, dated Mar. 4, 2009, 2 pages.
Invalidity Suit by KCI Medizinprodukte GmbH versus Kalypto Medical, Inc., concerning declaration of invalidity of the German part of the European Patent No. 2021046 (German application No. 602007021330.4) dated Mar. 11, 2015 in 66 pages. EP2021046 is related to the present application by virtue of a common priority claim to U.S. Appl. No. 11/432,855, now U.S. Pat. No. 7,615,036, and U.S. Appl. No. 11/610,458, now U.S. Pat. No. 7,779,625.
Jeter K F., et al., "Managing Draining Wounds and Fistulae: New and Established Methods," Chronic Wound Care, Chapter 27, 1990, pp. 240-246.
Johnson F.E., "An Improved Technique for Skin Graft Placement using a Suction Drain, Surgery, Gynecology and Obstetrics," Dec. 1984, pp. 584-585 (3 pages).
Kalypto Medical, "NPD 1000 Negative Pressure Wound Care System," Clinician & Patient Instructions for Use, Feb. 2010, 36 pages.
Kalypto Medical, NPD 1000 Product Brochure (publication date unknown, believed to be Nov. 2010), 4 pages.
KCI Inc., "If It's Not V.A.C. Therapy, It's Not Negative Pressure Wound Therapy," KCI Brochure, Jan. 2005, 5 pages.
KCI Licensing Inc, "Prevena™ Incision Management System—Clinician Guide—Instructions for Use," 390061 Rev D, Jan. 2010, 10 pages.
KCI, "Prevena—Incision Management System Patient Guide," Jan. 2010, 2 pages.
KCI, "V.A.C. Freedom User's Guide," May 2002, 16 pages.
Kendall Ultec Hydrocolloid Dressing (4×4"), Product Ordering Page, web page downloaded on Jul. 13, 2014, 1 page.
Khirugii V., "A Collection of Published Studies Complementing the Research and Innovation of Wound Care," The Kremlin Papers, Perspectives in Wound Care, Russian Medical Journal, Blue Sky Publishing, 2004, pp. 2-17.
Kostiuchenok B.M., et al., "The Vacuum Effect in the Surgical Treatment of Purulent Wounds," Russian Journal: Vestnik Khirurgii, Sep. 1986, pp. 18-21.
Landes R.R., et al., "An Improved Suction Device for Draining Wounds," Arch. Surg., vol. 104, May 1972, p. 707.
Landis E.M., et al., "The Effects of Alternate Suction and Pressure on Blood Flow to the Lower Extremities," Alternate Suction and Pressure, J Clin Invest, Sep. 1993, vol. 12 (5), pp. 925-961.
Linden, W.V.D., et al., "Randomized Trial of Drainage After Cholecystectomy: Suction Versus Static Drainage Through a Main Wound Versus a Stab Incision," American Journal of Surgery, Feb. 1981, vol. 141, pp. 289-294.
McFarlane R.M., "The Use of Continuous Suction under Skin Flaps," British Journal of Plastic Surgery, 1958, pp. 77-86.
McLaughlan J., et al., "Sterile Microenvironment for Postoperative Wound Care," The Lancet, Sep. 2, 1978, pp. 503-504.
Meyer D.C., et al., "Weight-Loaded Syringes as a Simple and Cheap Alternative to Pumps for Vacuum-Enhanced Wound Healing," Plastic and Reconstructive Surgery, Jun. 2005, vol. 115(7), pp. 2174-2176.
Mitchell R.N., et al., "Role of Stem Cells in Tissue Homeostasis," Pocket Companion to Robbins and Cotran Pathologic Basis of Disease, 7th Edition, 2006, p. 55 (3 pages).
Morykwas M.J., et al., "Nonsurgical Modalities to Enhance Healing and Care of Soft Tissue Wounds," Journal of the Southern Orthopaedic Association, vol. 6, No. 4, 1997, pp. 279-288.
Morykwas M.J., et al., "Vacuum-Assisted Closure: A New Method for Wound Control and Treatment: Animal Studies and Basic Foundation," Annals Plastic Surgery, vol. 38 (6), Jun. 1997, pp. 553-562.
Nakayama Y., et al., "A New Method for the Dressing of Free Skin Grafts," Plastic and Reconstructive Surgery, vol. 86(6), Dec. 1990, pp. 1216-1219.
Notice of Opposition—Statement of Facts and Evidence of the European Patent No. 2214610, dated Jul. 8, 2019, 18 pages.
NURSING75., "Wound Suction: Better Drainage with Fewer Problems," Oct. 1975, pp. 52-53.
NURSING75., "Wound Suction: Better Drainage with Fewer Problems," vol. 5(10), Oct. 1975, pp. 52-55.
Opponent's Written Submission in Preparation for the Oral Proceedings, for the Opposition of European Patent No. 2214610, dated Sep. 25, 2020, 5 pages.
Proprietor's Written Submission in Preparation for the Oral Proceedings, for the Opposition of European Patent No. 2214610, dated Oct. 1, 2020, 20 pages.
Protz K., "Modern Wound Dressings Support the Healing Process," Wound care: Indications and Application, Geriatrie Journal, Apr. 2005, pp. 3333-3339 (17 pages with English translation).
Ramirez O.M., et al., "Optimal Wound Healing Under Op-Site Dressing," Ideas and Innovations, vol. 73 (3), May 9, 1983, pp. 474-475.
Ranson, J.H.C., et al., "Safer Intraperitoneal Sump Drainage," Surgery, Gynecology & Obstetrics, Nov. 1973, vol. 137, pp. 841-842.
Reply of the Patent Proprietor to the Notice of Opposition, re the Opposition of European Patent No. 2214610, dated Dec. 3, 2019, 25 pages.
Reply to Opponent's Submission dated Jul. 13, 2022, for European Patent No. 2214610, mailed on Nov. 9, 2022, 6 pages.
Sames C.P., "Sealing of Wounds with Vacuum Drainage", British Medical Journal, Nov. 5, 1977, p. 1223.
Smith & Nephew, "PICO Single Use Negative Pressure Wound Therapy System," Spiral Booklet, Mar. 2011, 7 pages.
Solovev V. A, et al., "The Method of Treatment of Immature External Fistulas in the Upper Gastrointestinal Tract—Guidelines," USSR Ministry of Health, S. M. Kirov Gorky State Medical Institute, 1987, 19 pages.
Solovev V.A., "Treatment and Prevention of Suture Failures after Gastric Resection," Dissertation Abstract, Gorky, 1988, 51 pages.
Statement of Grounds of Appeal for the Opposition of European Patent No. 2214610, mailed on Mar. 8, 2022, 49 pages.
Stewart J., "World Wide Wounds—Next Generation of Products for Wound Management," Nov. 2002, http://www.worldwidewounds.com/2003/april/Stewart/Next-Generation-Products.html, 13 pages.
Summons to attend oral proceedings pursuant to Rule 115(1) EPC for Patent No. EP2214610, mailed on Feb. 19, 2021, 17 pages.
Svedman P., "A Dressing Allowing Continuous Treatment of a Biosurface," IRCS Medical Science: Biomedical Technology; Clinical Medicine; Surgery and Transplantation, vol. 7, 1979, p. 221.
Svedman P., et al., "A Dressing System Providing Fluid Supply and Suction Drainage Used for Continuous or Intermittent Irrigation," Annals of Plastic Surgery, vol. 17 (2), Aug. 1986, 9 pages.
Svedman P., "Irrigation Treatment of Leg Ulcers," The Lancet, Sep. 3, 1983, pp. 532-534.
Swift S., et al., "Quorum Sensing in Aeromonas Hydrophila and Aeromonas Salmonicida: Identification of LuxRI Homologs AhyRI and AsaRI and Their Cognate N-Acylhomoserine Lactone Signal Molecules," Journal of Bacteriology, Sep. 1997, vol. 179, No. 17, pp. 5271-5281.
Technology Watch, May 1989, 1 page.
Teder H., et al., "Continuous Wound Irrigation in the Pig," Journal of Investigative Surgery, 1990, vol. 3, pp. 399-407.
The Free Dictionary, "Flap Valve," Webster's Revised Unabridged Dictionary, retrieved from http://www.thefreedictionary.com/flapper+valve , published 1913 by C. & G. Merriam Co, 2 pages.
Tribble D E., "An Improved Sump Drain-Irrigation Device of Simple Construction," Archives of Surgery, vol. 105, Sep. 1972, pp. 511-513.
Usupov Y. N., et al., "Active Wound Drainage," Russian Journal: Vestnik Khirurgii, Apr. 1987 (p. 42-45), Perspectives in Wound Care, BlueSky Publishing, pp. 8-10.

(56) References Cited

OTHER PUBLICATIONS

Venturi M L., et al., "Mechanisms and Clinical Applications of the Vacuum-Assisted Closure (VAC) Device," Am J Clin Dermatol, 2005, vol. 6, No. 3, pp. 185-194.
Viljanto J., et al., "Local Hyperalimentation of Open Wounds," Br. J. Surg., vol. 63, 1976, pp. 427-430.
Wackenfors A., et al., "Effects of Vacuum-Assisted Closure Therapy on Inguinal Wound Edge Microvascular Blood Flow," Wound Repair and Regeneration, vol. 12, No. 6, Nov.-Dec. 2004, pp. 600-606.
Webb L X., "New Techniques in Wound Management: Vacuum-Assisted Wound Closure," Journal of the American Academy of Orthopaedic Surgeons, vol. 10, No. 5, Sep./Oct. 2002, pp. 303-311.
Westaby S., et al., "A Wound Irrigation Device," The Lancet, Sep. 2, 1978, pp. 503-504.
Wooding-Scott M., et al., "No Wound is Too Big for Resourceful Nurses," RN, Dec. 1988, pp. 22-25.
Written Submission by the Opponent re the Opposition Proceedings for European Patent No. 2214610, mailed on Aug. 4, 2021, 2 pages.
Written Submission by the Proprietor re the Opposition Proceedings for European Patent No. 2214610, mailed on Aug. 6, 2021, 23 pages.
Wu S.H., et al., "Vacuum Therapy as an Intermediate Phase in Wound Closure: A Clinical Experience," Eur J Plast Surg, 2000, vol. 23, pp. 174-177.

\* cited by examiner

VACUUM ASSISTED WOUND DRESSING

CROSS-REFERENCE TO RELATED APPLICATIONS

This application is a continuation of U.S. application Ser. No. 17/360,893, filed Jun. 28, 2021, which is a continuation of U.S. application Ser. No. 15/973,111, filed May 7, 2018, which is a divisional application of U.S. application Ser. No. 14/254,807, filed Apr. 16, 2014, which is a continuation application of U.S. application Ser. No. 12/744,055, filed May 20, 2010, which is a U.S. National Phase of the PCT International Application No. PCT/GB2008/051088 filed on Nov. 20, 2008, designating the United States and published on May 28, 2009 as WO 2009/066104, which claims priority to Great Britain Patent Application No. 0722820.8, filed Nov. 21, 2007. The disclosure of these prior applications is incorporated by reference in their entirety and should be considered a part of this specification.

BACKGROUND OF THE INVENTION

Field of the Invention

The present invention relates to a topical negative pressure (TNP) assisted wound dressing particularly, though not exclusively, for the treatment of wounds of relatively low area and/or relatively low volume.

The subject of this invention is an apparatus for the management of small to medium sized wounds that utilises a vacuum source but manages wound exudate in a traditional manner by utilising an absorbent self-cohesive material in the wound cavity. No fluid is exported from the locality of the wound cavity other than by local evaporation. In this manner, an extremely portable system, of minimal inconvenience to the wearer, can be generated.

Background to the Invention

TNP therapy has enjoyed relatively recent commercial success. WO9605873 and its family members describes a portable TNP therapy apparatus. The apparatus described mechanically supports tissue in the vicinity of the wound site and tissue mechanics and the rate of exudation from such sites requires a system such as that described in WO9605873 or as described in patents such as GB2378392 and WO2005/082435 which have remote waste receptacles to which wound exudate fluid is aspirated in order to cope with the volume of fluids generated in a relatively short time, less than that period in which a dressing would normally be left in place. However, for wounds of surface area below approximately 200 cm$^2$ or internal volumes below about 1000 cm$^3$ these solutions may not be the most appropriate since exudate volumes and exudate rates from these wounds may be managed by more traditional wound dressings, requiring dressing change every 3-7 days. The relatively small dimensions of such wounds do not make them attractive for the traditional TNP therapies disclosed in the prior art; these devices typically including a remote vacuum source, fluid transfer lumen and remote fluid collection receptacle, control and power source and are of dimensions and weight exceeding those convenient or discrete for the patient to carry.

The general principles of TNP apparatus described in the prior art comprise a fluid-permeable wound cavity filling element, a dressing for covering the wound and providing a reasonably air-tight seal around the wound, a drainage tube connecting the wound site and cavity filling element to the vacuum source via a fluid collection canister. The precise nature of the wound filling element has been the subject of much invention in this field. The mode of action of the apparatus is the application of negative pressure to the wound cavity, causing compression of the wound cavity filler and expansion of the surrounding tissue into the wound cavity. Wound exudate is drawn from the surrounding tissue, through the still porous cavity filler, along the drainage tube and into the remote collection receptacle. An important feature of the prior art is the ability of the wound cavity filler to remain sufficiently porous, when compressed under negative pressure, to allow fluid transport from the tissue to the drainage or aspirant tube. Porosity can be facilitated at the molecular level, for example in a hydrogel, or at the microscopic level, for example in a hydrocellular foam. To facilitate fluid flow, a hydrophobic filling has been deemed particularly desirable by workers in the field and absorbent fillers as being particularly undesirable due to their hindering fluid transport.

In contrast to the principles of TNP therapy, the general principle of traditional wound dressings is the localisation of wound exudate at the locality of the wound, either within the wound cavity or in close proximity to the surface. For this purpose, extremely absorbent materials are desirable that retard the free flow of fluid, preferably absorbing the fluid and localising it. Aquacel (trade mark) made by ConvaTec Ltd is an example of a non-woven dressing that absorbs substantial quantities of fluid and effectively locks it in the dressing. Allevyn (trade mark) made by Smith & Nephew Ltd is an example of a foam dressing that absorbs substantial quantities of fluid while allowing rapid transpiration through a high moisture vapour permeable top-film.

SUMMARY OF SOME EXEMPLIFYING EMBODIMENTS

In summary, the prior art deals exclusively with vacuum assisted fluid transport away from the site of the wound. A very broad range of wound cavity filling and contacting elements have been described and exemplified in the prior art, including materials commonly used in traditional wound care dressings. Without exception in these cases, the cavity filling and wound contacting elements act as a conduit for the transport of fluid from the wound per se to a remote collection canister via an aspirant tube connected to a vacuum source.

An object of the present invention is to overcome or reduce the limitations of the prior art for the management of wounds of low surface area, particularly those below approximately 200 cm$^2$ or internal volumes below 1000 cm$^3$, while not resorting to the exclusive use of traditional absorbent dressings. A further object of the present invention is to overcome or minimise the problem of vacuum device portability.

According to a first aspect of the present invention there is provided apparatus for the application of topical negative pressure therapy to a wound site, the apparatus comprising: a wound contacting element for retaining wound exudate fluid therein; a wound covering element that provides a substantially airtight seal over the wound contacting element and wound site; a vacuum connection tube connecting the wound contacting element to a vacuum source; and a vacuum source connected to a distal end of the vacuum connection tube.

The wound contacting element essentially blocks liquid transport beyond itself under pressures between atmospheric pressure and 200 mmHg below atmospheric pressure. Preferably, the wound contacting element material blocks liquid transport beyond itself at pressures of up to 250 mmHg below atmospheric pressure.

This invention concerns apparatus including a dressing for the management of wounds. In contrast to current therapies and prior art in the field of TNP therapy, the invention provides a system that, while exposing the wound to the many benefits of TNP, does not allow the export of wound fluid from the confines of the wound cavity. The apparatus relies upon a wound contacting element that does not allow the transport of fluid beyond itself under the range of negative pressures being applied to the wound.

A particular advantage of the apparatus according to the present invention is that confinement of wound fluid to the immediate vicinity of the wound enables the provision of an extremely small and light and consequently highly portable vacuum source and a convenient simple coupling and decoupling means of the vacuum source to the wound site dressing and which overcome significant limitations in the usability and portability of prior art apparatus.

In the present specification the term 'wound contacting element' means the portion of the apparatus/dressing filling the wound cavity or covering the wound. The nature of the wound contacting element is not restricted, provided that its composition or structure is able to essentially block the flow of exudate away from itself under the pressure range specified above.

For example, the wound contacting element may include a liquid-triggered valve that closes when it becomes in contact with a liquid. Such a valve may be situated proximate to the vacuum tube connection point at the wound covering element. Thus, when contacted by liquid the valve closes and no liquid is transported by the vacuum tube. The valve may be an electromechanical valve or a smart valve comprised of a water-absorbent material that expands to close within a constriction upon contact with liquid. The water-absorbent material may be placed within a restricted aperture within the valve. The wound contacting element positioned between such a valve and the wound may be absorbent or non-absorbent but may preferably be absorbent. The filling, in this embodiment, may be any medically-suitable composition such as, for example, a gauze, a foam, a woven, a non-woven, knit or moulded material.

Alternatively, the wound contacting element may comprise entirely, or in part, a suitable material structured such that it can absorb wound exudate but does not allow transmission of this fluid to the vacuum tube. This configuration is defined by two parameters: the aperture of the exit(s) from the material constituting the wound contacting element and the mechanical integrity of the material when wet. For example, an absorbent material that becomes laden with exudate must not itself be displaced along the vacuum connection tube. This is a particular problem with particulate or fibrous so-called superabsorbent materials, for they can pass, even when fully saturated with fluid, through very small apertures of a size below which vacuum levels cannot be efficiently maintained. In effect this means that the narrower the tube transmitting the vacuum, the greater the loss in vacuum pressure with distance from the vacuum source, which loss in negative pressure is negligible for macroscopic bores but can be significant as bores reduce below 1 mm diameter. To overcome these problems, an absorbent material with substantially enhanced self-cohesive properties compared to those currently available is described in our co-pending patent application GB0719065.5 of common ownership herewith.

When an absorbent material is included in the wound contacting element, the absorbent material not necessarily acting as a fluid transport blocking element, the material may preferably be capable of absorbing more than 5-times its own weight in fluid, more preferably more than 10-times its own weight in fluid and more preferably still more that 15-times its own weight in fluid. Such high w/w fluid absorbency may be desirable so that the wound can be initially dressed with a low weight material thereby reducing stress on the wound and the patient.

One group of materials particularly suited for this purpose are so-called superabsorbent materials, for example, those based on polycationic or polyanionic polymers. Superabsorbent polyanionic polymers include polyacrylic acid salts and polyacid derivatives of polysaccharides, such as carboxyalkylcellulose, or structural derivatives. Preferably, when the material is polyanionic, it may be a polyacrylic acid salt or derivative or carboxymethylcellulose or derivative. Preferably, when the material is polycationic, it may be chitosan-based, more preferably a carboxyalkylchitosan or derivative, even more preferably carboxymethylchitosan.

One particularly preferred material is a superabsorbent material capable of self-coalescence upon fluid absorption (see our GB0719065.7 the content of which is included herein by reference). These materials are able to effectively block the transport of liquid beyond their boundaries and also do not themselves flow or disaggregate under the influence of negative pressure or at the levels of externally applied physical stresses resulting from the negative pressure within a wound cavity.

A preferred material attribute may be the ability to achieve rapid haemostasis in the event of bleeding in the wound site.

A further preferred material attribute may be the ability to kill pathogens, such as bacteria or fungi, which come into contact with it. Preferably the material is inherently antimicrobial.

Carboxyalkylchitosan-based materials are suitably both haemostatic and antimicrobial.

The wound contacting element material can be provided in any form suitable to enable fluid ingress and absorption but to block the flow of fluid away from the wound contacting element. Suitable designs include dispersions of superabsorbent particles within a network of wicking fibres (as utilised in diapers, for example) or reticulated or discontinuous material comprising the superabsorbent material, such as open celled foams, knits, laminates, woven or non-woven materials. Preferably, the material may be in the form of a non-woven sheet for application to largely two-dimensional wounds or non-woven balls for application to largely three-dimensional wound cavities.

The wound covering element may be any material substantially impermeable to the flow of liquid, but may or may not be substantially permeable to the transmission of water vapour. The wound covering element is preferably a highly conformable transparent material which may optionally be coated with, or be manufactured such that, the side contacting the wound contact element and the patient's skin may be considered adhesive to the skin. Here, adhesive is taken to mean able to stay in place in the absence of negative pressure. Suitable materials for the manufacture of a highly conformable transparent wound covering include polyurethanes, polyolefins, polyacrylates, silicone-based polymers or composites comprising any combination of these materials.

The wound covering element may be a traditional wound dressing, for example composed of an absorbent foam, for example, Allevyn (trade mark) made by Smith & Nephew Medical Limited or non-absorbent film such as Tegaderm (trade mark) made by 3M Inc.

The wound covering element may be optionally provided with a means of connecting the vacuum connection tube with the wound covering element by, for example, a central or radial aperture or apertures in the wound covering element. The wound contacting element may be connected, via the wound covering element, to the vacuum connection tube by any means known to the skilled person including luer fittings such as commercially available valves and ports, magnetic couplings or adhesive sheet or tape. The connection of the vacuum tube to the wound covering element may preferably be achieved via a non-adhesive elastomeric cup positioned at the end of the vacuum connection tube and a pressure-sensitive valve positioned in the wound covering element itself. The pressure-sensitive valve may open when a pressure differential of a specified magnitude exists over its two surfaces such as between 5 and 200 mmHg, for example. The material comprising the elastomeric cup and pressure-sensitive valve may preferably be a silicone-based material. It is desirable that the coupling system is suitable for repeated coupling and uncoupling, as convenient for the patient.

Optionally, these coupling elements may be impregnated or coated with antimicrobial materials including, but not restricted to, antibiotics, silver compounds or materials, iodine-based formulations, polyhexamethylene biguanide, triclosan or chlorhexidine. Preferably, the elements may be coated with silver clusters.

The vacuum connection tube may be any of appropriate mechanical properties and bore for the transmission of negative pressure from the vacuum source to the wound contacting element. However, dependent upon the configuration of the wound contacting element, the bore of the tube may be such that it is incapable of transmitting dry or hydrated components of the wound contacting element. The tubing may be as conformable and light weight as possible and may be coiled or linear. The tubing may be single or multi-lumen, or a combination of lumens, and may optionally split and or rejoin to form separate tubular elements for the management of a single wound site or multiple wound sites. The tubing may be opaque or transparent.

The wound contacting element and wound covering element may be optionally combined into a single element.

The wound covering element and vacuum connection tube may optionally be combined into a single element.

The wound contacting element, wound covering element and vacuum connection tube may be optionally combined into a single element.

The vacuum source may be any available and may be optionally mechanically powered by, for example, a compressed spring and comprise a syringe as the vacuum generating means as is known in the prior art; or electrically powered, for example a vacuum pump. Preferably, the vacuum source may be capable of generating vacuums in the range of −10 mmHg to −250 mmHg relative to atmospheric pressure. More preferably, the vacuum source is a vacuum pump capable of generating vacuums in the range of −10 mmHg to −250 mmHg relative to atmospheric pressure. The pump may generate a vacuum by any convenient means; diaphragm pumps, peristaltic pumps, Venturi-effect pumps and other displacement pumps may be suitable for this purpose.

The vacuum source may preferably be below 500 g in weight, more preferably below 100 g in weight and even more preferably below 50 g in weight.

In cases where the vacuum source is electrically powered, the power source may be mains supplied, a battery supply or a locally generated supply such as a clockwork generator, a solar cell, a thermo cell or a kinetic autorelay type of power source. Preferably the power source may be a battery.

In cases where the power source is a battery, the battery may be disposable or rechargeable. When the battery is rechargeable, recharging may be achieved via a charging station for the vacuum housing or for the battery itself. Battery life may be preferably longer than 12 hours, more preferably longer than 24 hours and even more preferably longer than 72 hours. The battery may preferably be below 100 g in weight, more preferably below 50 g in weight.

The power and vacuum sources may be housed separately or together. Preferably they are housed together. When housed, the combined weight of the power and vacuum source and housing may be preferably less than 1 kg, more preferably less than 500 g, more preferably still less than 200 g. The housing may be of any geometry but is preferably adapted so as to be convenient for the patient and/or carer to handle and carry. It may also preferably be of dimensions below 15×15×6 cm.

The apparatus of the first aspect of the present invention may be applied to wounds for their management. The general principle of the apparatus is the application of the wound contacting element to the wound, covering the wound contacting element with the wound covering element and coupling the wound contacting element to a vacuum source via a vacuum connection tube. As mentioned above, two or more of these elements may be provided as a single entity. Preferably for largely two-dimensional wounds, the wound contacting element and the wound covering element may be a single entity. This combined entity may contain the pressure-sensitive valve in its top surface and may be attached to the perimeter of the wound by appropriate means. Attachment of the dressing to a patient may be achieved by the application of negative pressure alone, in the absence of a bonding means or may be achieved via a bonding means. Attachment may preferably be achieved by a bonding means, for example a pressure sensitive adhesive applied to the skin contacting surface of the wound covering element. When the bonding means is a pressure sensitive adhesive, it may preferably be a poly(acrylate)- or silicone-based formulation.

According to a second aspect of the present invention there is provided apparatus for the application of topical negative pressure therapy to a wound site, the apparatus comprising: a wound covering element that provides a substantially airtight seal over the wound; a vacuum connection tube connecting the wound covering element to a vacuum source; a vacuum source connected to a distal end of the vacuum connection tube; the wound covering element having valve means associated therewith which permits only fluid flow out of a wound cavity defined by the wound covering element and the wound.

When the wound contacting element and the wound covering element are in place, the vacuum source is activated and the vacuum connection tube, preferably attached to the vacuum source, may be connected to the wound covering element via an aperture or valve in the wound covering element. At any point during the application of negative pressure therapy, the coupling of vacuum connection tube to the wound covering element can be reversibly broken and re-established at the convenience of the patient or carer.

In an embodiment of the apparatus according to either the first or second aspects of the present invention the dressing wound covering element may comprise a one-way valve as mentioned above, the valve essentially being able to allow fluid in the form of air to be withdrawn from the wound cavity defined by the wound covering element via the vacuum connection tube. As mentioned above the vacuum connection tube may preferably be repeatably connectable and disconnectable to the dressing/wound covering element without damage thereto such that the vacuum source may be removed by the patient and the dressing left in place but sealed against the ingress of bacteria and potential infection, for example, by the presence of the one-way valve in the wound covering element.

The one-way valve means may be a simple plastics material self-sealing valve as are available commercially for many diverse applications outside of the field of TNP therapy such as those sold under the trade mark "miniValve" by Mini Valve International, for example.

Desirably the vacuum connection tube may be attached to the dressing/wound covering element by non-adhesive means so as to facilitate repeated connection/disconnection thereof without damaging the wound covering element film material. In this regard the vacuum connection tube may be connected by "sucker" means at the dressing end of the vacuum connection tube, the sucker means being, for example, in the form of a cup-shaped, domed or bell-shaped conformable plastics material member which is in fluid communication with the vacuum connection tube and which member which may be placed over the valve means in the wound covering element and seal with surrounding wound covering element material, the sucker means being held in place on the dressing/wound covering element by the vacuum generated by the vacuum source itself. Disconnection of the vacuum connection tube may then be effected merely by turning off the power source to the vacuum source or by breaking the seal of the sucker by lifting its edge (NB the sucker can easily be removed by this intentional manipulation but cannot easily be accidentally dislodged by vertical extensive force e.g. pulling on the vacuum connection tube).

When the wound contacting element becomes saturated with wound exudate, the vacuum connection tube can be disconnected and the wound contacting element and wound covering element (or a physical combination of the two) can be exchanged for a new set.

Wounds suitable for management by the apparatus that is the subject of this invention include injuries to soft and hard tissue, including the skin, muscle, cartilage, tendons, bone and internal organs.

In the second aspect of the invention a wound contacting element of highly absorbent material may not be present and wound exudate may be aspirated from the wound cavity to a remote waste receptacle by the vacuum source.

BRIEF DESCRIPTION OF THE DRAWINGS

In order that the present invention may be more fully understood examples will now be described by way of illustration only with reference to the accompanying drawings, of which.

DETAILED DESCRIPTION OF SOME EXEMPLIFYING EMBODIMENTS

Figure 1:
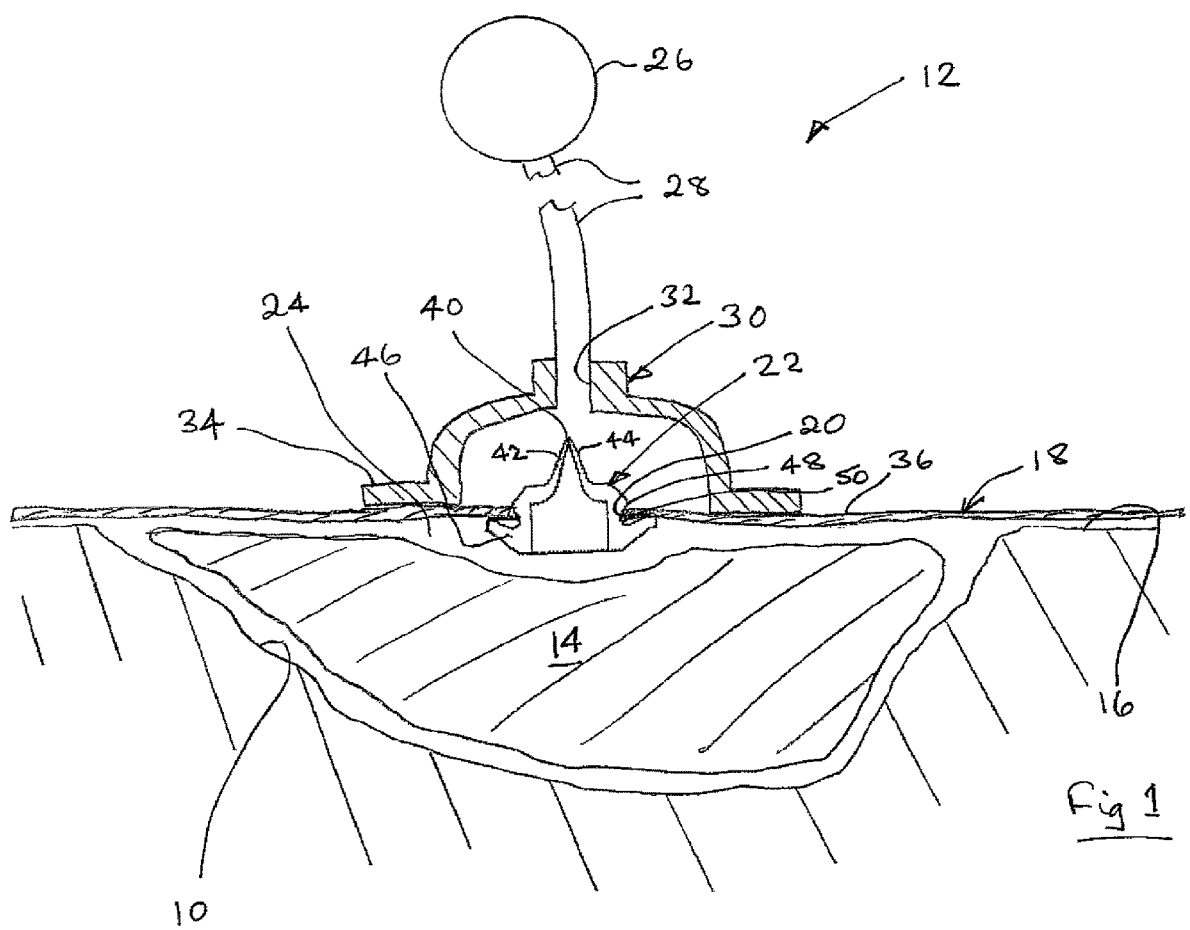
FIG. 1 shows a schematic cross section of an embodiment of apparatus according to the present invention and a wound being treated by TNP therapy.

Referring now to the drawings and where the same features are denoted by common reference numerals.

FIG. 1 shows a schematic cross section through a wound 10 having an embodiment of apparatus 12 according to the present invention applied to it for the purpose of TNP therapy of the wound. The wound 10 has a wound contacting element 14 placed in the cavity defined by the wound, the wound contacting element being roughly level with surrounding sound skin 16. A wound covering element 18 is applied over the wound to contact and seal with the surrounding sound skin by means of a layer of pressure sensitive adhesive (not shown) coated onto the skin contacting surface of the wound covering element material. The wound covering element 18 has an aperture 20 in the area above a part of the wound and the wound contacting element 14. A one-way valve 22 is positioned in the aperture 20 to permit fluid in the form of air to be extracted from the wound cavity 24 defined by the wound covering element 18 and the wound 10 itself. A vacuum source 26 in the form, in this example, of a battery powered vacuum pump is connected to the wound cavity by a vacuum connection tube 28 and a cup-shaped connection member 30 having an aperture 32 therein to accept the end of the vacuum connection tube 28. The cup-shaped member 30 has a flange portion 34 which seats onto the upper surface 36 of the wound covering element 18 material and seals therewith. The valve 22 has an orifice 40 which is normally closed due to the resilience of the material from which it is moulded, for example, silicone plastics based material. The orifice 40 is in the form of a slit normally closed by two lips 42, 44 (the shape of the valve orifice may be likened to a flat bladed screwdriver and the valve orifice 40 in FIG. 1 runs normal to the plane of the page). The valve 22 is initially held in and sealed to the wound covering element material 18 by a flange portion 46 bearing against the underside of the wound covering element 18 material and a circular shoulder 48 and recess 50 which is held in the aperture 20. To evacuate the wound cavity 24, the vacuum pump 26 is started and the cup-shaped member 30 placed on the wound covering element material above the valve 22 and the reduction in pressure within the wound cavity 24 causes the cup-shaped member 30 to be sealed securely to the dressing by the excess pressure of the surrounding ambient air. As the vacuum in the wound cavity develops, the wound covering element 18 is pushed down against the wound contacting element 14 by ambient air pressure and the wound contacting element 14 compressed against the wound surface to apply TNP therapy thereto.

Whilst it is perfectly feasible for the lower surface of the flange portion 34 of the cup-shaped member 30 to be adhesively coated and to be so retained on the wound covering element material, in this example retention of the vacuum connection tube 28 to the wound dressing is solely by ambient air pressure as described above. In case the patient wishes to detach the vacuum pump 26 and leave it behind this may simply be achieved by turning off the pump 26 and allowing the vacuum to degrade and removing the cup-shaped connection member 30. In this case the valve 22 is self-sealing prevents access of bacteria and the like to the wound cavity 24.

The valve 22 exemplified above is a miniValve (trade mark) supplied by Mini Valve International. However, this valve is merely exemplary and many other types of suitable valves are available commercially.

For example International Patent Application No PCT/EP2008/063046 discloses a composition which coalesces on hydration and which can be used to provide a valve which closes upon contact with liquid. The application is included fully herein by way of reference but briefly discloses a suitable composition that enables a new physical transformation. The physical transformation in question involves the conversion of a first stable physical geometry into a second stable physical geometry upon hydration, wherein hydration enables the self-coalescence (fusion) of spatially separated elements or surfaces of the first stable physical geometry.

Each geometry is physically stable. Thus, immersion of the first stable physical geometry in excess solution results in conversion to the second stable physical geometry without significant loss of the material mass by dissolution. That is, the second stable geometry is insoluble, or has only very limited solubility, in the excess solution. The second stable physical geometry is, at least substantially, self supporting such that it is able to retain its shape when is excess solution, or when removed therefrom. In typical preferred forms in the second stable physical geometry the material of the invention is a gel or gel like material.

A feature of the composition is the physical homogeneity of the object in both the first and second physical geometries.

The novel transformation is enabled by construction of the object, at least in part, from materials that can exist in physically stable forms in the dry state and the hydrated state. Furthermore, the hydrated state of the material must be sufficiently self-cohesive, even when immersed in excess solvent, to enable fusion to occur. This, we believe, is a property unique to a limited range of states of matter, some of which we prepare to exemplify this invention.

In broad terms the composition of matter when formed into an object of suitable geometry, can self-coalesce upon hydration in a suitable solvent.

According to a first aspect of the composition there is provided a high molecular mass cationic polymer material having a first state which includes at least two separate but adjacent surfaces and a second state in which the polymer consists of a homogeneous body, wherein the material transitions from the first state to the second state upon hydration.

Thus, on hydration the material expands and the surfaces merge or coalesce to result in a body of self supporting material, typically a gel or gel-like material, which has uniform properties in any dimension. Surfaces and other boundaries within the body of material are absent. Furthermore the body of material is insoluble, or at least of limited solubility in the hydrating solvent and is able to retain its physical geometry under leading (for example gravity).

The term 'suitable geometry' is taken to describe an arrangement where separate (for example spatially separate, but not necessarily physically separate) elements or surfaces of the object are sufficiently proximate to enable coalescence upon hydration-induced expansion.

The term 'suitable solvent' is taken to describe a fluid (liquid or gas) that can be absorbed be the object, causing expansion and a change in the physical properties of the object (e.g. surface energy). The suitable solvent is typically and preferably an aqueous medium.

The term 'self-coalesce' is taken to describe the transformation of two or more spatially separated physically homogeneous elements into a single physically homogeneous element or of fusion of previously spatially separated surfaces of the same element.

Suitable compositions of matter from which objects can be formed are those comprised, entirely or in part, of high average molecular weight cationic polymers including zwitterionic (carrying both anionic and cationic charge) polymers with a cationic charge bias. The cationic polymer may be, or may be a derivative of, a synthetic or a naturally occurring polymer. Preferably, the cationic polymer is one carrying amine functionality. More preferably, the cationic polymer is a polysaccharide. More preferably still, the cationic polymer is chitosan or a derivative of chitosan. The chitosan may be derived from any source, marine or fungal, and is preferably of a weight average molecular weight (Mw) exceeding kDa (kilodaltons), more preferably exceeding 100 kDa and most preferably exceeding 200 kDa.

Where the polymer is a derivative of chitosan, it is preferably a carboxylated derivative. More preferably, it is a carboxyalkyl derivative of chitosan. More preferably still, it is a carboxymethyl derivative of chitosan. The carboxymethyl derivative of chitosan is preferably of a weight average molecular weight exceeding 50 kDa, more preferably exceeding 100 kDa, especially exceeding 500 kDa, more especially exceeding 600 kDa and especially 700 kDa or more.

Carboxymethylation is preferably achieved using known reagents: a base and chloroacetic acid or preferably a neutral salt of chloroacetic acid such as sodium chloroacetate. Preferably, the reaction is carried out in a single step: chitosan fibres or (less preferably) particles being immersed in a solution of reagents or vice versa. Suitable reaction solvents include mixtures of an alcohol with water. The alcohol may be any known but is preferably a non-solvent for chitosan and carboxymethylchitosan, for example isopropanol. The base may be any known but is preferably a water-soluble inorganic base such as sodium hydroxide or potassium hydroxide, preferably sodium hydroxide.

According to a second aspect of the composition there is provided a method of preparing high molecular mass carboxymethylchitosan comprising the steps:

a. mixing chitosan with a solution of a base and chloroacetic acid, or a neutral salt thereof, dissolved in a reaction solvent comprising a mixture of an alcohol and water;

b. allowing the reaction to proceed at ambient temperature for at least 8 hours whilst ensuring adequate exposure of the chitosan to the reaction solvent;

c. when the reaction is complete, washing the reaction product in excess alcohol-containing solvent;

wherein the volume (in millilitres) of the reaction solvent is at least 20-times the mass (in grams) of chitosan.

A high molecular mass carboxymethyl chitosan preferably comprises a carboxymethyl chitosan having a mass of at least 500 kDa, more especially at least 600 kDa and especially 700 kDa or more.

In one preferred embodiment the volume of reaction solvent (in millilitres) exceeds the mass of chitosan (in grams) by more than 20 but less than 70-times, more preferably by more than 30-times but less than 40-times.

In another preferred embodiment the mass of sodium chloroacetate exceeds the mass of chitosan by not more than 2-times, more preferably by not more that 1.2-times.

In a preferred embodiment, the alcohol of the reaction solvent is isopropanol.

In further preferred embodiments the reaction is carried out at ambient temperature for a period of at least 8 hours, more preferably for at least 15 hours and even more preferably for at least 18 hours.

In a particularly preferred embodiment, the alcohol of the reaction solvent is isopropanol, the mass of sodium chloroacetate is not more than twice (more especially not more than 1.2 times) the mass of the chitosan and the reaction is allowed to proceed for at least 8 hours.

When the chitosan is provided for reaction in powder or fibre form, this material should be adequately exposed to the turbid reaction solvent throughout the duration of the reaction. This process can be facilitated by any means known to the artisan but can be simply achieved by rolling the reaction vessel, for example.

When the reaction is complete, reaction by-products detrimental to the stability of the product, such as sodium chloride or sodium hydroxyacetate, should be removed to the maximum extent feasible. To achieve this, the reaction product is washed, preferably in one or more steps, in excess solvent comprised of at least 60 parts alcohol (such as ethanol) and 40 parts water (60:40).

More than one washing step is preferred and, when this is the case, the first wash step has preferably a higher water content than subsequent steps, with water content decreasing in every wash step. For example, a suitable two-step wash procedure involves a first wash in excess solvent comprised of at least 60 parts ethanol and 40 parts water (60:40) and a second wash in excess solvent comprised of at least 90 parts ethanol and 10 parts water (90:10).

Thus in a preferred embodiment the reaction product is washed in a plurality of washing stages, each employing an excess of a solvent comprising alcohol and water, wherein in each succeeding stage the solvent consists of a higher proportion of alcohol. Preferably the alcohol is ethanol It is essential that wash solvents always includes some water to avoid excessive dehydration of the product, which can result in brittleness.

The composition of the wash solvent may include any suitable alcohols such as ethanol, isopropanol or methanol. Ethanol is preferred.

The product resulting from washing and solvent removal can be sterilised by methods typical for the sterilisation of medical devices, for example gamma-irradiation, electron-beam irradiation or ethylene oxide treatment.

Prior to radiation-based sterilisation, the washed reaction product should be adequately solvent-free. This can be achieved by any drying process known to the skilled artisan. A preferred drying process is conducted at temperatures not exceeding 40° C., more preferably not exceeding 30° C. Preferably, solvent removal is achieved by placing the material under a sub-atmospheric pressure. The pressure is preferably less than 500 mbar, more preferably less than 1000 mbar. The duration of the drying process, when achieved by vacuum drying, preferably exceeds 8 hours, more preferably exceeding 12 hours.

The weight average molecular weight of the material following washing and radiation sterilisation is preferably greater than 120 kDa, more preferably greater than 130 kDa and after washing and ethylene oxide sterilisation is preferably greater than 400 kDa, more preferably greater than 500 kDa. It is important that these molecular weights are obtained to avoid mechanical integrity problems in the final product and dissolution problems when exposed to fluid.

Additives and co-components can be added at any stage of the above process, prior to terminal sterilisation. These agents may be any suitable for a topical or internal medical application, such as analgesics, anaesthetics, antimicrobial agents, anti-cancer agents, nicotine or nicotine substitutes or other synthetic or naturally-derived pharmaceuticals including peptides, proteins such as growth factors or retardants, enzymes (e.g. those facilitating tissue debridement), DNA or RNA fragments.

When the additive is an antimicrobial agent, it may be for example: silver or silver compounds, iodine or iodine compounds, quaternary amine-based antimicrobials such as polyhexamethylenebiguanide or chlorhexidene, antibiotics such as gentamycin, vancomycin or a peptide-based agent.

When silver is introduced into the formulation, and the formulation is carboxymethylchitosan-based, addition is preferably achieved by immersion in a solvent mixture of a similar composition as that applied during the carboxymethylation process.

In a third aspect, the composition can be used to provide a method of fusing two or more solid surfaces, wherein the surfaces are initially separate (in particular, spatially separated) but adjacent surfaces of one or more object(s) comprising a self-coalescing material as herein described, notably the high molecular mass polymer material of the first aspect of the invention. The method comprises the step of immersing said surfaces in an aqueous medium and thus hydrating and expanding the self-coalescing material. In one embodiment, the surfaces are initially spatially separated surfaces of the same object. Alternatively, the surfaces are initially spatially separated surfaces of different objects. These alternatives are not mutually exclusive. The surfaces may be the surfaces of fibres, for example in a woven or, more especially, a non-woven fibrous material. In such materials, the surfaces may have portions which are spaced apart and portions which, while being separate, are in contact.

Objects fabricated from the compositions defined above, and suitable for the method, need to be suitably designed to enable coalescence upon hydration. For example, an isolated linear object would not have the opportunity to self-coalesce upon hydration. In contrast, a pair of isolated but adjacent linear objects would have the opportunity to swell and coalesce upon hydration. In this context, 'adjacent' means located within about 10 mm of one another. Thus, suitable objects can be defined as containing, at least in part, spatially separated elements or surfaces located within about 10 mm of one another. Preferably, the spatially separated elements or surfaces are located within 5 mm of one another. More preferably, the spatially separated elements or surfaces are located within 1 mm of one another. In some cases, for example fibre based materials, at least parts of adjacent surfaces may be in contact.

Preferred physical formats that meet the above description are fibre-based materials such as woven and non-woven materials. Other suitable formats include knits, open-celled foams and laminates including corrugated materials. More complex arrangements can be fabricated by methods known to one skilled in the art, such as lithography, micromachining and electrospinning. The composition and its uses is not restricted to formats of high open area but includes solid monoliths. Fibre based materials are preferred and fibre-based non-woven materials are particularly preferred.

The composition in use is not restricted to objects consisting exclusively of self-coalescent material, but includes composites, for example composites of common medical device formats and self-coalescent material and surface-coatings, for example implantable metal- or biomaterial based devices including soft-tissue substitutes and joint implants. Composites suitable for topical and internal wound management include those combining polyurethane based materials, such as foams, slabs and films with self-coalescent materials, for example in powdered or, more especially, fibrous form.

When devices comprised, at least in part, of the compositions are immersed in a fluid, they absorb fluid, become swollen and self-coalesce across contact points. Use is not restricted to specific compositions or specific fluids, but in preferred forms and for preferred end-sues, the fluid is most preferably water based. For example, in the case of carboxymethylchitosan-based materials, the fluid is preferably water based. Examples of water based fluids include water or a solution of water, such as saline or a biologically-derived fluid such as whole blood, blood plasma, serum, saliva, wound exudate or bone marrow aspirate.

The novel material properties of the described self-coalescing materials can be exploited in a range of applications, for example in irreversible fluid valving systems and moulding materials.

EXAMPLES

Example 1

Generation of Self-Coalescing Carboxymethylchitosan Fibres

A) Synthesis

Immediately prior to reaction, sodium chloroacetate (1.75 g) was dissolved in 4% aqueous sodium hydroxide solution (7 ml). This solution was added to isopropanol (45 ml) and shaken vigorously, resulting in a turbid suspension. This mixture was added to a vessel containing chitosan fibres (1.50 g), the container sealed and rolled at approximately 60 rpm for 18 hours.

B) Washing Steps

B1) After step A, the fibres were removed from the now clear reaction solvent and transferred to a vessel containing 99:1 ethanol:water (200 ml). The material was disturbed every 15 minutes for 1 hour, after which time the material was removed and physically dried by the application of hand pressure between several layers of absorbent material. Following gross drying, the material was vacuum dried at ambient temperature overnight.

B2) After step A, the fibres were removed from the now clear reaction solvent and transferred to a vessel containing 60:40 ethanol:water (200 ml). The material was disturbed every 15 minutes for 1 hour, after which time the material was removed and transferred to a second vessel containing 90:10 ethanol:water (200 ml). The material was disturbed every 15 minutes for 1 hour, after which time the material was removed and physically dried by the application of hand pressure between several layers of absorbent material. Following gross drying, the material was vacuum dried at ambient temperature overnight.

Example 2

Generation of Self-Coalescing Carboxymethylchitosan Fibres (Scale-Up)

Immediately prior to reaction, sodium chloroacetate (96.8 g) was dissolved in 4% aqueous sodium hydroxide solution (387 ml). This solution was added to isopropanol (2490 ml) and shaken vigorously, resulting in a turbid suspension. This mixture was added to a vessel containing chitosan fibres (83.0 g), the container sealed and rolled at approximately 60 rpm for 18 hours. After this time, the fibres were removed from the now clear reaction solvent and transferred to a vessel containing 99:1 ethanol:water (2000 ml). The material was disturbed every 15 minutes for 1 hour, after which time the material was removed and physically dried by the application of hand pressure between several layers of absorbent material. Following gross drying, the material was vacuum dried at ambient temperature overnight.

Example 3

Radiation Sterilisation of Self-Coalescing Carboxymethylchitosan Fibres

The material resulting from Example 1, step B2 was packaged in gas-permeable sterilisation pouches and sterilised by gamma irradiation at 30-40 kGy. The molecular weight of the material pre- and post-sterilisation was determined by gel permeation chromatography. The molecular weight prior to sterilisation was approximately Mw 700 kDa; the molecular weight post-sterilisation was approximately Mw 140 kDa. The molecular weight change in the material, although substantial, was such that the physical properties of the material were not significantly altered by sterilisation.

Example 4

Ethylene Oxide Sterilisation of Self-Coalescing Carboxymethylchitosan Fibres

The material resulting from Example 1, step B2 was packaged in gas-permeable sterilisation pouches and sterilised by ethylene oxide treatment. The molecular weight of the material pre- and post-sterilisation was determined by gel permeation chromatography. The molecular weight prior to sterilisation was approximately Mw 700 kDa; the molecular weight post-sterilisation was approximately Mw 575 kDa. The molecular weight change in the material was such that the physical properties of the material were not significantly altered by sterilisation.

Example 5

Water Absorbency of Self-Coalescing Carboxymethylchitosan Fibres

The material resulting from Example 3 (100 mg) was immersed in water (4 ml) for 1 minute and withdrawn. Excess liquid was allowed to drain and then the hydrated transparent mass was weighed. The material was calculated to absorb approximately 25-times its own mass in water without significant dissolution.

Example 6

Serum Absorbency of Self-Coalescing Carboxymethylchitosan Fibres

The material resulting from Example 3 (100 mg) was immersed in serum (4 ml) for 1 minute and withdrawn. Excess liquid was allowed to drain and then the hydrated transparent mass was weighed. The material was calculated to absorb approximately 13-times its own mass in serum without significant dissolution.

Example 7

Self-Coalescence of Carboxymethylchitosan Fibres in Water

The material resulting from Example 3 (100 mg) was immersed in water (4 ml) for 1 minute and withdrawn. Excess liquid was allowed to drain and then the hydrated transparent mass was allowed to stand for 4 hours. After this time, the individual fibres of the material had self-coalesced and the material was then effectively a homogeneous, elastic hydrogel, able to stably retain its physical geometry under loading (FIG. 2).

Example 8

Self-Coalescence of Carboxymethylchitosan Fibres in Serum

The material resulting from Example 3 (100 mg) was immersed in serum (4 ml) for 1 minute and withdrawn. Excess liquid was allowed to drain and then the hydrated transparent mass was allowed to stand for 4 hours. After this time, the individual fibres of the material have self-coalesced and the material as effectively a homogeneous, elastic hydrogel, able to stably retain its physical geometry under loading.

Figure 2A:
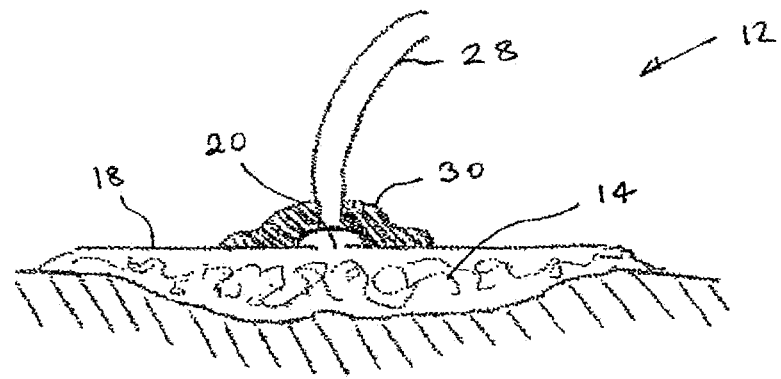
FIGS. 2A to 2C which show the arrangement of FIG. 1 simplified and the progression of saturation of a wound contacting element.
Figure 2B:
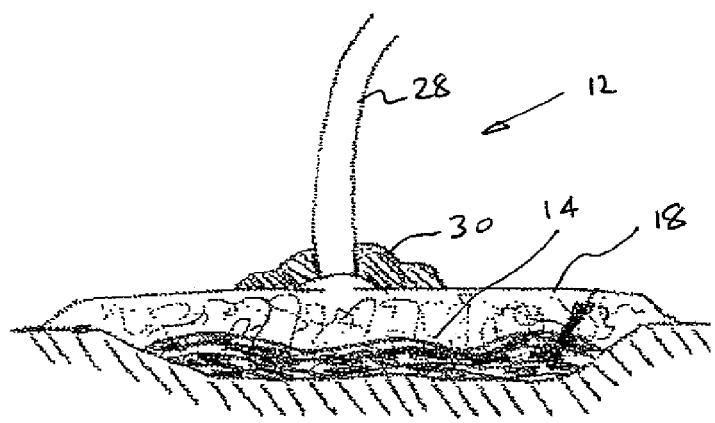
Figure 2C:
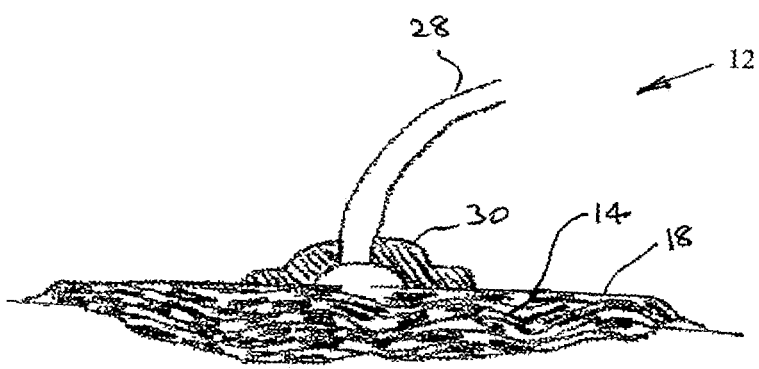

FIGS. 2A to 2C show stages in the absorption of wound exudate into the wound contacting element 14. The basic arrangement may be the same as that of FIG. 1, however, the drawings of FIG. 2 have been simplified. FIG. 2A shows a clean dressing newly installed in the wound 10 and without any exudate being taken up; FIG. 2B shows the wound contacting element 14 partially full of exudate; and, FIG. 2C shows the wound contacting element 14 saturated with wound exudate. However, the nature of the wound contacting element material 14 is such that no liquid is aspirated by the vacuum connection tube 28 out of the wound cavity 24 or indeed out of the wound contacting element 14 itself.

Figure 3:
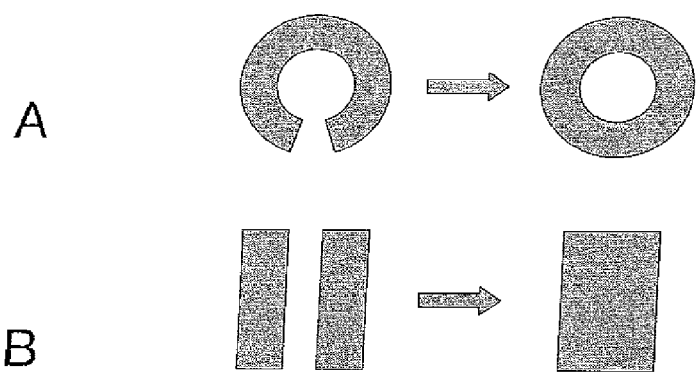
FIG. 3 illustrates a liquid contact triggered valve.

FIG. 3 shows paradigms of the conversion of a first stable physical geometry into a second stable physical geometry upon hydration, wherein hydration enables the self-coalescence (fusion) of spatially separated elements of the first stable physical geometry. In case A, the self-coalescence comprises the fusion of spatially separated surfaces of a single element; in case B the surfaces are adjacent surfaces of two separate elements.

The Examples described below are based on the use of the apparatus arrangement shown in FIG. 1 and/or FIG. 2 and/or FIG. 3.

Example 1

Application of apparatus of FIG. 1 to ex vivo cavity wound. A 5 cm diameter, 5 cm depth cavity wound was cut by scalpel into a porcine leg joint. The musculature in the area of the wound cavity was injected with saline to ensure that the tissue was adequately hydrated for the duration of the experiment. The wound cavity was packed with two wound contacting elements of non-woven balls of carboxymethylchitosan fibre and the wound cavity and filling was covered over with an adhesive silicone gel sheet Cica-Care (trade mark) made by Smith & Nephew Medical Ltd with a central 5 mm diameter aperture 20. A luer loc fitting attached to a coiled vacuum hose was inserted through the aperture and connected to a battery-powered vacuum source Pac-Vac (trade mark) made by Virtual Industries Inc. Immediate contraction of the wound margin was observed and the non-woven balls were compressed down to be flush with the surface of the skin. The system was left in place for 8 hours undisturbed, after which time no fluid had exited the cavity packing but had collected within it.

Example 2

Assembly of apparatus based on FIG. 1 having a wound covering element 14 of Allevyn Adhesive (trade mark) made by Smith & Nephew Medical Ltd.

A 3 mm diameter aperture in the top film of Allevyn Adhesive was created using a biopsy punch. Over this aperture was bonded a silicone elastomer dome miniValve (trade mark) made by Mini Valve International B. V., part number DO 072.004. A miniature vacuum source made by Virtual Industries Inc., PAC-VAC V3200 (trade mark) was coupled by vacuum tubing 28 to a hand-made silicone rubber cup 30.

Example 3

Usage of apparatus based on Allevyn Adhesive as in Example 2. A 5 cm diameter, 5 cm depth cavity wound was cut by scalpel into a porcine leg joint. The musculature in the area of the wound cavity was injected with saline to ensure that the tissue was adequately hydrated for the duration of the experiment. The wound cavity was packed with wound contacting element 14 comprising two non-woven balls of carboxymethylchitosan fibre and the wound cavity 24 and filling was covered over with the modified Allevyn Adhesive dressing described in Example 2. The vacuum source, as described in Example 2, was turned on and the vacuum tubing cup placed over the dome valve positioned centrally on the Allevyn Adhesive. Immediate contraction of the Allevyn Adhesive dressing and the wound margin was observed and the non-woven balls were compressed down to be flush with the surface of the skin. The system was left in place for 8 hours undisturbed, after which time no fluid had exited the cavity packing but had collected within it.

Example 4

Usage of apparatus based on Allevyn Adhesive as described in Example 2. A 5 cm diameter, 5 mm depth shallow wound was cut by scalpel into a porcine leg joint. The musculature in the area of the wound was injected with saline to ensure that the tissue was adequately hydrated for the duration of the experiment. The wound was covered with a non-woven sheet of carboxymethylchitosan as the wound contacting element 14 and the wound and non-woven sheet was covered over with the modified Allevyn Adhesive dressing described in Example 2 as the wound covering element 18. The vacuum source, as described in Example 2, was turned on and the vacuum tubing cup placed over the dome valve positioned centrally on the Allevyn Adhesive. Immediate contraction of the Allevyn Adhesive dressing was observed. The system was left in place for 8 hours undisturbed, after which time no fluid had exited the wound dressing but had collected within it.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. An apparatus for the application of topical negative pressure therapy, the apparatus comprising:

a wound covering element configured to be positioned over a wound, the wound covering element comprising an aperture;

a cup-shaped port seated onto a surface of the wound covering element over the aperture; and a self-coalescing liquid-retaining layer positioned under the wound covering element, the liquid-retaining layer configured to retain wound exudate therein upon application of negative pressure.

2. The apparatus of claim 1, wherein the liquid-retaining layer is configured to inhibit wound exudate from being aspirated through the aperture.

3. The apparatus of claim 1, further comprising a vacuum connection conduit configured to be connected to the wound covering element.

4. The apparatus of claim 1, wherein the wound covering element further comprises an adhesive configured for adhering to a portion of skin surrounding the wound.

5. The apparatus of claim 1, wherein the liquid-retaining layer is configured to be positioned at the aperture.

6. The apparatus of claim 1, wherein the liquid-retaining layer comprises self-coalescing fibers.

7. The apparatus of claim 1, wherein the wound covering element and the liquid-retaining layer are combined into a single element.

8. The apparatus of claim 1, wherein the liquid retaining layer comprises superabsorbent particles.

9. The apparatus of claim 1, wherein the liquid-retaining layer comprises wicking fibers.

10. The apparatus of claim 1, wherein the cup-shaped portion comprises a flange.

11. The apparatus of claim 1, wherein at least a portion of the liquid-retaining layer is configured to transform into a gel upon contact with wound exudate.

12. A method for the application of topical negative pressure therapy, the method comprising:

applying a wound covering element over a wound, the wound covering element comprising an aperture positioned under a cup-shaped port; and delivering negative pressure to the wound from a source of negative pressure;

wherein a self-coalescing liquid-retaining layer is positioned in a flow-path between the wound covering element and the source of negative pressure, the liquid-retaining layer configured to retain wound exudate therein upon application of negative pressure.

13. The apparatus of claim 12, further comprising inhibiting wound exudate from being aspirated through the aperture.

14. The apparatus of claim 12, further comprising connecting a vacuum connection conduit configured to the wound covering element.

15. The apparatus of claim 12, wherein the wound covering element further comprises an adhesive configured for adhering to a portion of skin surrounding the wound.

16. The apparatus of claim 12, wherein the liquid-retaining layer comprises self-coalescing fibers.

17. The apparatus of claim 12, wherein the liquid retaining layer comprises superabsorbent particles.

18. The apparatus of claim 12, wherein the wound covering element and the liquid-retaining layer are combined into a single element.

19. The apparatus of claim 12, wherein the wound covering element further comprises an adhesive to adhere the wound covering element to a portion of skin surrounding the wound.

20. The apparatus of claim 12, wherein the liquid-retaining layer comprises wicking fibers.

* * * * *